(12) United States Patent
Mauger

(10) Patent No.: US 11,123,510 B2
(45) Date of Patent: Sep. 21, 2021

(54) RESPIRATOR DEVICES WITH SOURCE CONTROL MECHANISMS AND ASSOCIATED SYSTEMS AND METHODS

(71) Applicant: O2-O2, INC., Brooklyn, NY (US)

(72) Inventor: Jeremy Mark Mauger, Auckland (NZ)

(73) Assignee: O2-O2, Inc., Brooklyn, NY (US)

( * ) Notice: Subject to any disclaimer, the term of this patent is extended or adjusted under 35 U.S.C. 154(b) by 0 days.

(21) Appl. No.: 17/027,566

(22) Filed: Sep. 21, 2020

(65) Prior Publication Data

US 2021/0077762 A1    Mar. 18, 2021

Related U.S. Application Data

(63) Continuation of application No. PCT/US2020/050458, filed on Sep. 11, 2020.

(30) Foreign Application Priority Data

Sep. 12, 2019    (NZ) ........................................ 757200

(51) Int. Cl.
| | |
|---|---|
| *A61M 16/06* | (2006.01) |
| *A61M 16/00* | (2006.01) |
| *A61M 16/10* | (2006.01) |
| *A61L 9/015* | (2006.01) |

(Continued)

(52) U.S. Cl.
CPC ......... *A61M 16/0616* (2014.02); *A61L 9/015* (2013.01); *A61L 9/20* (2013.01); *A61L 9/22* (2013.01); *A61M 16/0003* (2014.02); *A61M 16/107* (2014.02); *A61M 16/1065* (2014.02); *A61L 2209/14* (2013.01); *A61L 2209/212* (2013.01); *A61M 2016/0027* (2013.01);
(Continued)

(58) Field of Classification Search
CPC ....... A62B 18/00; A62B 18/02; A62B 18/045; A62B 7/10; A61B 18/003; A42B 3/286; A61M 16/06; A61L 9/20; A61L 9/22
See application file for complete search history.

(56) References Cited

U.S. PATENT DOCUMENTS

| | | |
|---|---|---|
| 3,004,535 A | 3/1960 | Nielson |
| 4,011,865 A | 3/1977 | Morishita |
| 4,037,593 A | 7/1977 | Tate, Jr. |

(Continued)

FOREIGN PATENT DOCUMENTS

| | | |
|---|---|---|
| BE | 555402 A | 2/1960 |
| CN | 103223214 A | 7/2013 |

(Continued)

OTHER PUBLICATIONS

U.S. Appl. No. 16/937,376, filed Jul. 23, 2020, Feasey et al.

(Continued)

*Primary Examiner* — Margaret M Luarca
(74) *Attorney, Agent, or Firm* — Perkins Coie LLP

(57) ABSTRACT

The present technology relates to respirator devices including source control features. In some embodiments, a source control mask device can include a shield that substantially covers the mouth and nose of a user and a mechanism that can actively extract air as it is exhaled by the user. The extracted exhaled air can then be sanitized before the mask device discharges it into the atmosphere. The mask device may selectively form a seal to the user's face dependent on air flow conditions.

23 Claims, 19 Drawing Sheets

(51) Int. Cl.
*A61L 9/20* (2006.01)
*A61L 9/22* (2006.01)

(52) U.S. Cl.
CPC ........... *A61M 2202/206* (2013.01); *A61M 2205/3334* (2013.01)

(56) References Cited

U.S. PATENT DOCUMENTS

| | | |
|---|---|---|
| 4,136,688 A | 1/1979 | Gorman |
| 4,233,972 A | 11/1980 | Hauff et al. |
| 4,331,141 A | 5/1982 | Pokhis |
| 5,357,947 A * | 10/1994 | Adler ............. A41D 13/1146 128/201.13 |
| 6,014,971 A * | 1/2000 | Danisch ............. A62B 18/045 128/201.25 |
| 6,119,689 A | 9/2000 | Korman |
| 8,733,356 B1 * | 5/2014 | Roth ............. A61L 9/20 128/205.27 |
| 10,758,751 B2 | 9/2020 | Feasey et al. |
| 2005/0028811 A1 * | 2/2005 | Nelson ............. A61M 16/06 128/200.11 |
| 2005/0103343 A1 | 5/2005 | Gosweiler |
| 2007/0163586 A1 | 7/2007 | Burnett et al. |
| 2007/0240716 A1 | 10/2007 | Marx |
| 2009/0210989 A1 | 8/2009 | Becker et al. |
| 2010/0031617 A1 | 2/2010 | Ensor et al. |
| 2011/0265790 A1 | 11/2011 | Walker et al. |
| 2014/0373846 A1 * | 12/2014 | Kao ............. A61F 9/02 128/204.23 |
| 2015/0256010 A1 | 9/2015 | Scandurra |
| 2018/0078798 A1 | 3/2018 | Fabian et al. |
| 2018/0296864 A1 | 10/2018 | Feasey et al. |
| 2019/0174845 A1 | 6/2019 | Cheng et al. |

FOREIGN PATENT DOCUMENTS

| | | | |
|---|---|---|---|
| CN | 203724660 U | 7/2014 | |
| CN | 103961822 A | 8/2014 | |
| GB | 2251173 | 7/1992 | |
| KR | 101460942 B1 | 11/2014 | |
| KR | 20150115588 A | 10/2015 | |
| KR | 20160057949 A | 5/2016 | |
| WO | WO-8701950 A1 * | 4/1987 | ........... A62B 18/025 |
| WO | 2013082650 A1 | 6/2013 | |
| WO | 2013156017 A1 | 10/2013 | |
| WO | 2015167098 A1 | 11/2015 | |
| WO | 2017065620 A1 | 4/2017 | |

OTHER PUBLICATIONS

Wang, Air Curtain Study: https://www.amca.org/UserFiles/file/Energy%20Initiative%20Web%20Pages/Air-%20Curtain%20Study(1).pdf, Jul. 25, 2014, 14 pages.

International Search Report and Written Opinion for International Application No. PCT/NZ2016/050169 dated Dec. 22, 2016, 21 pages.

International Preliminary Report on Patentability for International Application No. PCT/NZ2016/050169 dated Feb. 14, 2018, 19 pages.

Supplementary European Search Report for Application No. EP16855822 dated Jun. 19, 2019, 11 pages.

International Search Report and Written Opinion dated Mar. 3, 2021; International Patent Application No. PCT/US2020/050458; 22 pages.

* cited by examiner

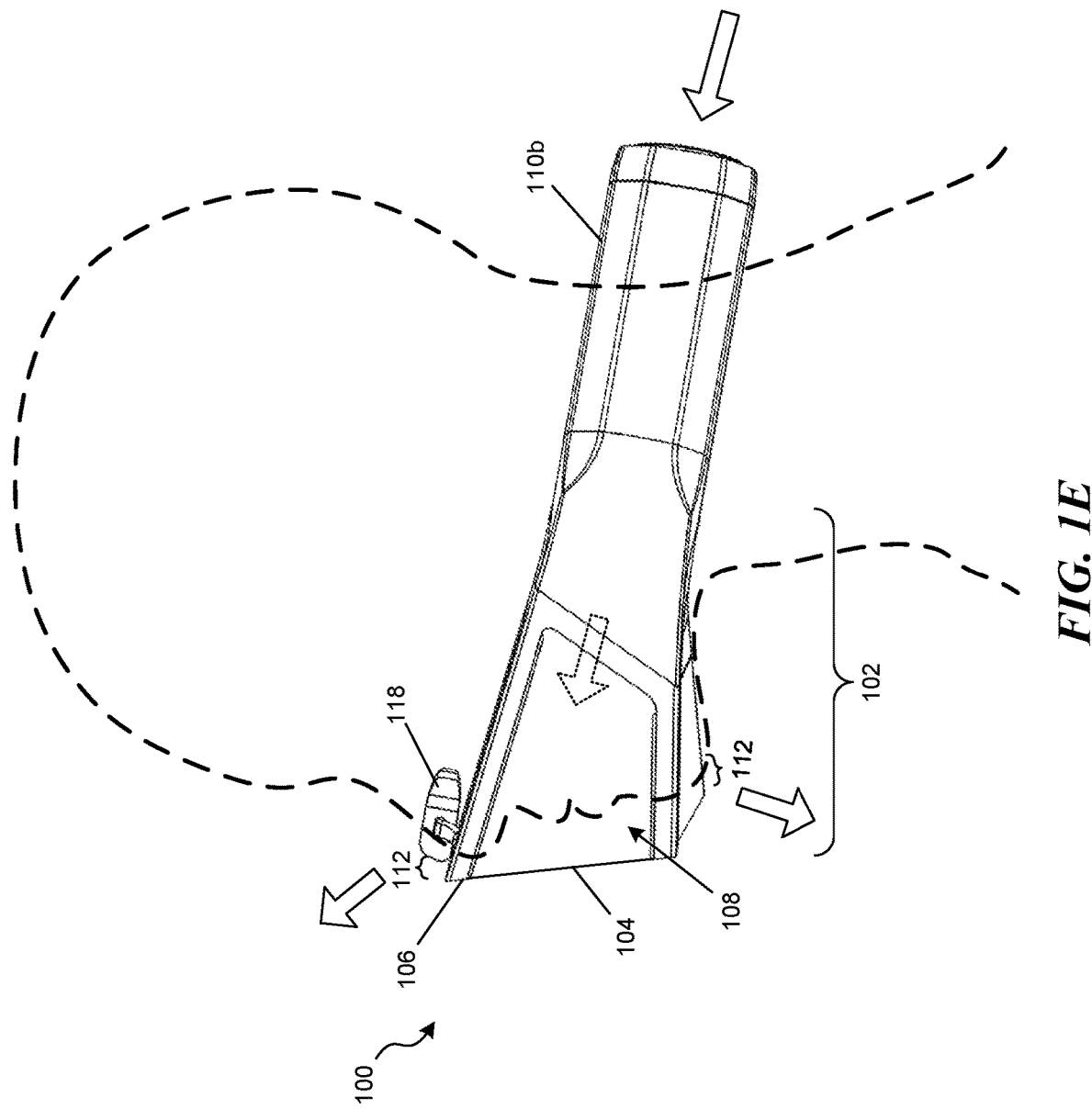

RESPIRATOR DEVICES WITH SOURCE CONTROL MECHANISMS AND ASSOCIATED SYSTEMS AND METHODS

CROSS-REFERENCE TO RELATED APPLICATION

This application is a continuation application of International Application No. PCT/US20/50458, filed Sep. 11, 2020, which claims priority to New Zealand Provisional Patent Application No. 757200, filed Sep. 12, 2019, both of which are incorporated herein by reference in their entireties.

TECHNICAL FIELD

The present technology generally relates to medical devices and, in particular, to respirator devices with source control mechanisms.

BACKGROUND

Air may contain numerous infectious pathogens such as viruses and bacteria. These pathogens commonly originate from exhalations of infected individuals. Airborne communicable diseases such as COVID-19, anthrax, chickenpox, influenza, measles, smallpox, cryptococcosis, and tuberculosis can be debilitating and even life-threatening. The control and the transmission of these diseases is costly, time consuming and ineffective. For example, the recent COVID-19 pandemic has had a global impact with devastating social, economic, and health consequences that are unprecedented in modern history.

Conventional face masks are frequently ineffective for preventing the transmission of airborne diseases. For example, homemade cloth masks can harbor pathogens and be less effective than wearing no mask at all. Surgical masks and industry dust masks do not provide a full seal against the user's face and are susceptible to leaking infectious material into the surrounding environment, particularly if the user coughs or otherwise breaks the mask's seal. Additionally, conventional face masks are typically uncomfortable to wear, unaesthetic, interfere with communication, and place an extra respiratory burden on the user, which frequently leads to poor user compliance and respiratory distress. Accordingly, improved respirator devices capable of preventing and containing the spreading of airborne communicable diseases are needed.

BRIEF DESCRIPTION OF THE DRAWINGS

Many aspects of the present technology can be better understood with reference to the following drawings. The components in the drawings are not necessarily to scale. Instead, emphasis is placed on clearly illustrating the principles of the present technology.

FIG. 1E is a side view of the respirator device of FIG. 1A.

DETAILED DESCRIPTION

A. Overview of the Technology

Figure 1A:
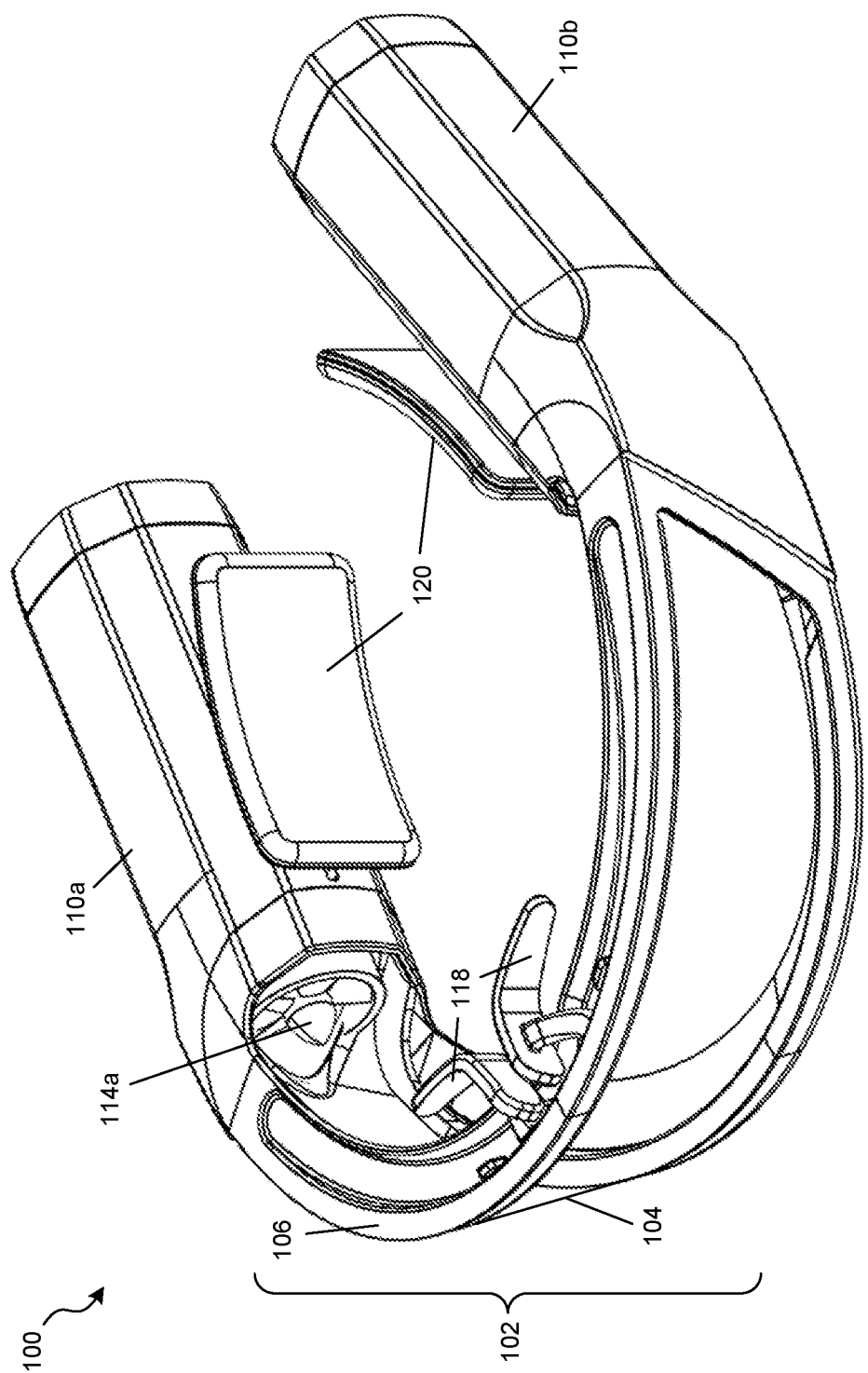
FIG. 1A is an isometric view of a respirator device configured in accordance with embodiments of the present technology.

The present technology is generally directed to respirator devices, and associated systems and methods. In some embodiments, a respirator device (also referred to herein as a "source control mask," "respiratory mask," or "device") is worn by a user known or suspected to have an airborne or aerosolized communicable disease. The respirator device can substantially or fully extend in front of (i.e., cover) the user's mouth and/or nose, and can include a powered system that actively extracts the air exhaled by the user. The respirator device can also include a source control mechanism that sanitizes the exhaled air before discharging it into the atmosphere. The mask may selectively form a seal to the user's face depending on the air flow conditions.

In some aspects of the present technology, a respirator device can include a mask section (also referred to herein as a "mask region" or "mask portion" or "mask component") defining a breathing chamber and configured to fit at least partially over a user's face (e.g., over the nose and mouth). The respirator device can also include an intake region fluidly coupled to the breathing chamber. Optionally, the intake region can include a filter or other mechanism for sanitizing air entering the breathing chamber from the external environment. The respirator device can further include a source control mechanism fluidly coupled to the breathing chamber and configured to sanitize air exiting from the breathing chamber to the external environment. For example, the source control mechanism can be a filter, an active sanitization mechanism (e.g., ultraviolet light, electrostatic precipitator), and/or any other apparatus configured to kill, inactivate, sterilize, filter, capture, and/or otherwise reduce or prevent infectious agents from entering the external environment. The respirator device also includes at least one fan unit configured to maintain an air flow path through the breathing chamber. The air flow path can include (i) an air inflow entering the breathing chamber via the intake region and (ii) an air outflow exiting the breathing chamber via the source control mechanism.

In some aspects of the present technology, a source control mask can include a face mask having a shield configured to cover at least a portion of the face of a user (e.g., the mouth and nose). The source control mask can also include a powered impeller unit mounted on the face mask and configured to create an area of low pressure in a breathing chamber or plenum of the mask. Atmospheric air can continually enter the breathing plenum across an engineered gap between the face and shield to create a negative-pressure seal for the prevention of infected air from entering the atmosphere. The air extracted from the breathing chamber is passed across a sanitization system to eradicate or reduce infectious agents therein.

In further aspects of the present technology, a source control attachment for a respirator mask is provided. The source control attachment can comprise a barrier component (e.g., a strip of material) that can be fastened along the perimeter of a mask shield and at least one filter medium or system. The attachment can be substantially located around the shield so as to seal the shield and a user's face. This source control attachment allows air to flow out of the higher pressure shield into the atmosphere while filtering, eradicating or reducing any infectious agents contained within the expelled air of the mask as it is breathed out by the user.

In other aspects of the present technology, a non-seal negative pressure mask is provided. The mask can be configured to capture most or all particulates that are emitted by the user's breath by using fans to create a continuous outflow of air into a sanitization and/or sterilization system. The sanitization/sterilization system can be or include nano-filter chambers having the ability to capture most or all of exhaled particles and pathogens by entrapment into nano-filters. The purified, clean air can then be released to the atmosphere without any or reduced infectious agents.

In further aspects of the present technology, a method of eradicating or reducing airborne communicable diseases is provided. The method includes utilizing and/or operating any of the respirator devices, source control masks, and/or source control mechanisms described herein. For example, the method can include positioning a respirator device at least partially over a face of a user having an infectious airborne disease (e.g., COVID-19), and operating the respirator device to sanitize air exhaled by the user.

The present technology is expected to address many shortcomings of conventional face masks. For example, seal-based masks such as N95 masks are generally designed to arrest airborne particulates from the environment to protect the user as they inhale. As a result, the resultant filtering of exiting air is dependent upon achieving and maintaining a tight seal between the mask and the user's face during inhalation, rather than during exhalation, particularly during heavy exhalation such as during exercise or coughing. Surgical masks are generally designed to capture, deflect, and dilute the concentration of aerosolized particles of the exhaled source breath in a purely mechanical way, without any assistance of filtration technology. Air supplying respirators typically are designed with a fan providing the wearer with clean breathable air through the filters and supply hoses connected to half or full-face masks or mouth pieces, with the exiting air not filtered in any way. Secure Fit masks manufactured by Crosstex are disposable surgical masks which provide additional buffers at the bottom and sides of the mask which can reduce exposure to infectious particulates. However, they are not suitable for respiratory source control.

While conventional face masks may provide some form of protection from sneezing droplets, they provide very little protection from airborne pathogens, especially during the breaking of the mask's seal during coughing. As a full seal is not provided, these face masks are susceptible to leakages of infectious material. In addition, individuals with respiratory problems or in critical conditions (especially patients) are rarely masked as it restricts personnel from monitoring their immediate conditions. Hence, in the majority of cases, the entire healthcare staff is masked and patient is unmasked. Therefore, when individuals are in the vicinity of an infectious patient, the risk of transmission is reduced only by the personal protective equipment of the individuals, not the infectious patient.

A further disadvantage that is well documented is the discomfort associated with wearing conventional face masks and the extra respiratory burden placed on the user. The user often is in a state of respiratory distress and this may lead to poor compliance, exacerbated respiratory condition(s), and/or heightened distress.

Furthermore, conventional technology such as medical breathing devices are comprised of large wired machines that are not portable. Further, like regular masks, medical breathing devices also obscure the user's face. In a hospital environment, this can be hazardous as this limits the communication between the patient and the healthcare worker.

Aesthetics can also be another important consideration. Conventional mask technology is typically industrial-based in its design and appearance, which may discourage user uptake and compliance.

From the above, it can be seen that there is a need for improvements to face masks and other respirator devices that prevent and contain the spreading of airborne pathogens (e.g., that cause communicable diseases, such as COVID-19) by sanitizing the exhaled air before discharging into the atmosphere. As described in further detail herein, the present technology provides one or more following: improved comfort for the user as it is lightweight; an engineered gap for breathing assistance and/or to enable natural breathing conditions (e.g., to relieve the user from expending more energy breathing relative to a closed system); battery-powered, hence portable; and/or a clear shield that allows for empirical observation of a patient's breathing conditions and health (e.g., color of the lips) and an enhanced ability to communicate with others. In addition, the overall source control face mask systems disclosed herein can provide a new type of patient monitoring in any healthcare settings, including both compliance and physiological state. As such, the respiratory masks disclosed herein can not only provide protection from infectious diseases, but can also provide for continuous monitoring on a localized level for each user. The present technology can also work simultaneously with health personnel who are wearing complementary face wear (e.g., a positive pressure mask) that is designed and styled to emulate the source control face mask versions, thereby creating a better patient experience. Beyond hospital or healthcare environments, the source control masks disclosed herein can also be very effective in situations where access to protective gear is limited, for example, in global pandemics and outbreaks of diseases. With the present technology, the transmission of airborne diseases can be reduced or prevented by only requiring infectious individuals to wear a source control mask, whereas conventional approaches and the economics of source control environments require everyone to wear some form of a mask. Further, source control attachment devices can be easily utilized and retrofitted to existing respirator masks.

Further aspects and advantages of the devices, methods, and uses will become apparent from the ensuing description that is given by way of example only.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1A-14B.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%. The term "substantially" or grammatical variations thereof refers to at least about 50%, for example, 75%, 85%, 95%, or 98%.

Although certain embodiments are described herein with reference to source control (e.g., source control mask, source control mechanism, source control skirt, etc.), this is not intended to be limiting, and the respirator devices described herein can be used by non-infected as well as infected individuals.

The headings provided herein are for convenience only and do not interpret the scope or meaning of the claimed present technology.

B. Selected Embodiments of Respirator Devices

Figure 1B:
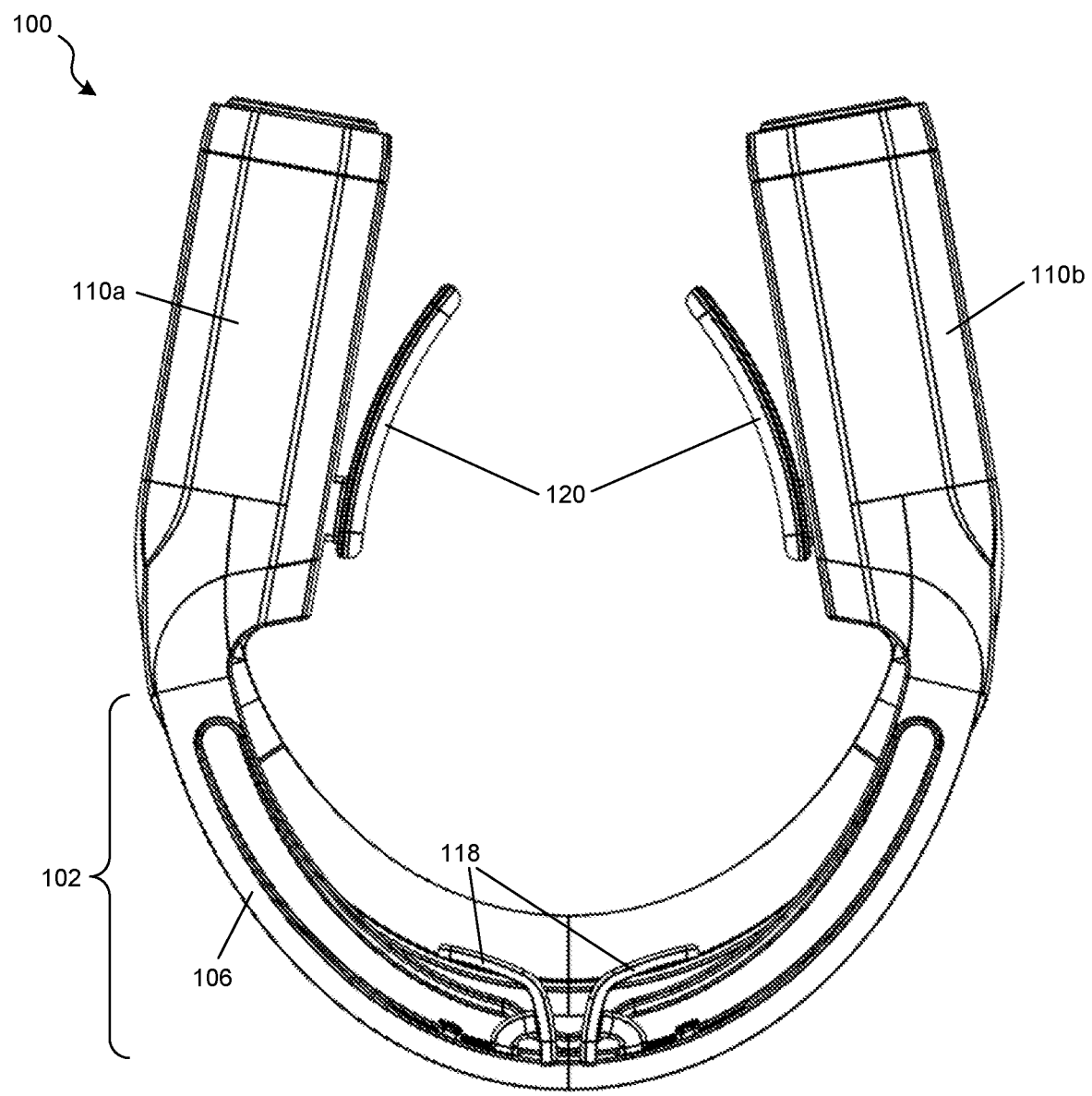
FIG. 1B is a top view of the respirator device of FIG. 1A.
Figure 1C:
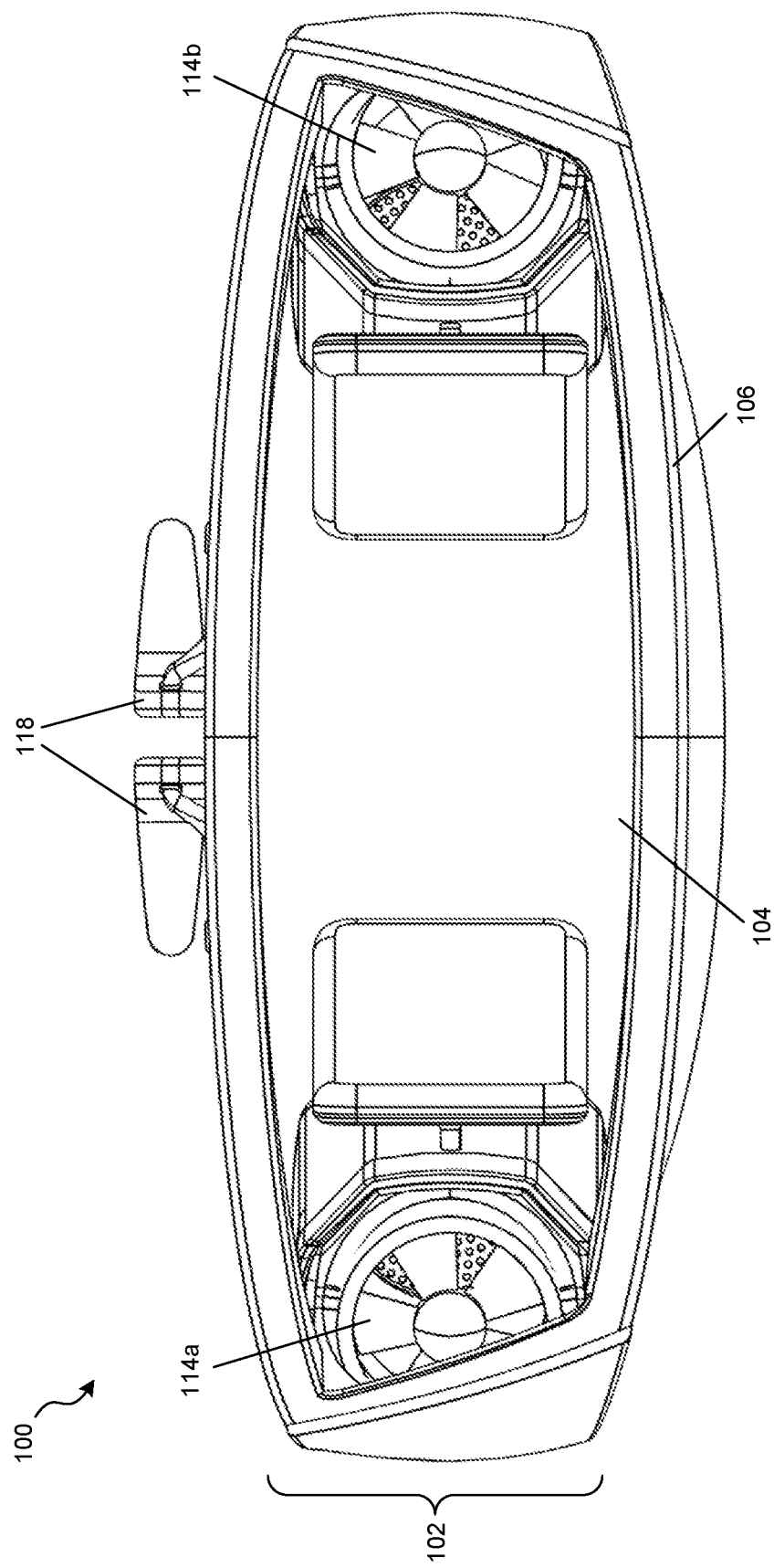
FIG. 1C is a front view of the respirator device of FIG. 1A.
Figure 1D:
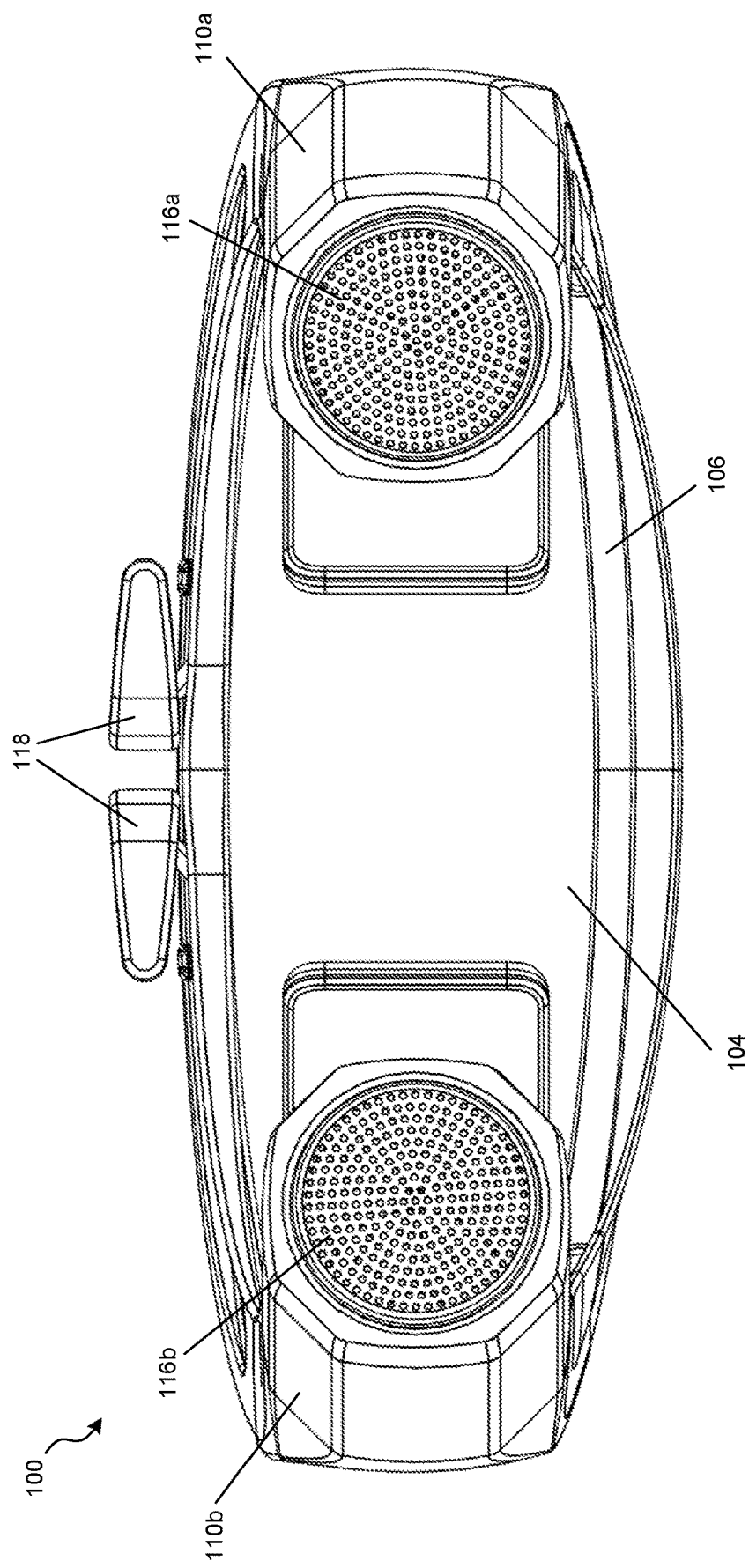
FIG. 1D is a back view of the respirator device of FIG. 1A.

FIGS. 1A-1E and the accompanying description provide a general overview of a representative respirator device 100 ("device 100") configured in accordance with embodiments of the present technology. More specifically, FIG. 1A is an isometric view of the device 100, FIG. 1B is a top view of the device 100, FIG. 1C is a front view of the device 100, FIG. 1D is a back view of the device 100, and FIG. 1E is a side view of the device.

Referring to FIGS. 1A-1E together, the device 100 includes a mask section 102 (also referred to as a "mask component") configured to partially or fully cover a user's face (e.g., a user's nose and/or mouth; best seen in FIG. 1E). The mask section 102 can have an elongated, curved shape that extends at least partially around and generally corresponds to the curvature of a human face. The mask section 102 can include a shield 104 configured to block air flow to and/or from the user's face. The shield 104 can be made out of any suitable air-impermeable material, such as plastic. For example, the shield 104 can be made of a thin plastic sheet or film, e.g., to reduce weight and/or improve sound transmission. For example, the shield 104 can be no more than 5 mm, 4.5 mm, 4 mm, 3.5 mm, 3 mm, 2.5 mm, 2 mm, 1.5 mm, 1 mm, 0.75 mm, 0.5 mm, 0.25 mm, or 0.1 mm in thickness. In the illustrated embodiment, the shield 104 is transparent, whereas in other embodiments the shield 104 can be opaque, partially opaque, or adjustable in transparency. One advantage of a transparent shield is that the user's face can be easily seen and monitored. For example, healthcare personnel or other individuals may monitor the user's face for visual indicators of the health condition such as pain, confusion, and/or vital signs (e.g., lip color). Additionally, a transparent shield can reduce interference with communication when wearing the device 100.

The shield 104 can be coupled to (e.g., mounted in or otherwise attached to) a frame 106. In the illustrated embodiment, the frame 106 surrounds the entire perimeter of the shield 104 (best seen in FIG. 1C). In other embodiments, the frame 106 can extend only around a portion of the perimeter of the shield 104 (e.g., only the top and bottom edges, only the lateral edges, etc.). The frame 106 can provide mechanical support to the shield 104, and can also serve as a connection point to other components of the device 100. In embodiments wherein the shield 104 is made of a relatively thin material (e.g., a thin plastic film), the frame 106 can be made of a rigid material that holds the shield 104 in tension in order to maintain its shape.

As shown in FIG. 1E, the mask section 102 defines and partially surrounds a breathing chamber 108 (also referred to as "plenum 108"). When the device 100 is worn by the user, the breathing chamber 108 is partially enclosed on one side by the internal surface of the shield 104 (i.e., the surface of the shield 104 facing the user) and on another side by the user's face. Accordingly, the user inhales air from the breathing chamber 108 and exhales air into the breathing chamber 108. In various embodiments, the device 100 is sized and shaped such that a peripheral region of the mask section 102, which can be defined by portions of the shield 104 and/or the frame 106, is spaced apart from the user's face by one or more gaps 112 (also referred to as "openings," "channels," "slots," and "vents"). The gaps 112 can each be approximately 0.25 cm, 0.5 cm, 0.75 cm, 1 cm, 1.25 cm, 1.5 cm, 2 cm, 2.5 cm, 3 cm, 3.5 cm, 4 cm, 4.5 cm, or 5 cm wide. Additionally, although FIG. 1E illustrates the gaps 112 as being at the upper and lower edges of the mask section 102, this configuration can be modified as desired (e.g., a single gap 112 at the upper edge, a single gap 112 at the lower edge, etc.).

In some embodiments, the device 100 is configured so that the air follows a defined air flow path through the breathing chamber, e.g., air enters the breathing chamber 108 from a specific air intake region and exits the breathing chamber 108 through a specific air outflow region. For example, air from the external environment can enter the breathing chamber 108 through lumens within one or more elongated arm members 110*a-b* (also referred to as "arms") coupled to one or both sides of the mask section 102 (FIGS. 1A and 1B), and can exit through the gaps 112 between the mask section 102 and the user's face. In other embodiments, however, the device 100 can have a different air flow path. For example, the air flow path shown in FIG. 1E can be reversed such that air enters the breathing chamber 108 through the gaps 112 and exits through the arms 110*a-b*.

The device 100 can include one or more fan units 114*a-b* (FIGS. 1A and 1C) to produce and/or maintain the air flow path through the breathing chamber 108. In the illustrated embodiment, the fan units 114*a-b* are mounted at least partially within the arms 110*a-b*, adjacent or near the breathing chamber 108. In other embodiments, however, the fan units 114*a-b* can be located at other portions of the device 100, as discussed in greater detail below. The fan units 114*a-b* can each be or include an impeller, rotor, or any other component configured to produce air flow. In some embodiments, the fan units 114*a-b* are each configured to produce an air flow rate greater than or equal to 10 L/min, 20 L/min, 30 L/min, 40 L/min, 50 L/min, 60 L/min, 70 L/min, 80 L/min, 90 L/min, 100 L/min, 125 L/min, 150 L/min, 175 L/min, 200 L/min, 225 L/min, 250 L/min, 275 L/min, or 300 L/min. The air flow rate may be varied, e.g., by changing the rotation speed of the fan units 114*a-b*.

Optionally, the fan units 114*a-b* can also be configured to maintain a desired pressure level in the breathing chamber 108 when the device 100 is worn. For example, the fan units 114*a-b* can be configured to maintain a positive pressure relative to the external environment, e.g., a positive pressure greater than or equal to 1 Pa, 2 Pa, 3 Pa, 4 Pa, 5 Pa, 6 Pa, 7 Pa, 8 Pa, 9 Pa, 10 Pa, 15 Pa, 20 Pa, 25 Pa, 30 Pa, 35 Pa, or 40 Pa. In some embodiments, the fan units 114*a-b* are configured to maintain a positive pressure relative to the external environment within a range from 5 Pa to 10 Pa during normal operation (e.g., while the user is exhaling at a normal rate), and within a range from 20 Pa to 30 Pa while the user is exhaling at a higher than normal rate (e.g., due to coughing, sneezing, heavy breathing, etc.). This can create a positive pressure seal that does not allow air from the external environment to enter through the gaps 112, thereby only allowing the user to breath filtered air entering the breathing chamber via the fan units 114, while still permitting exhaled air to exit via the gaps 112. In various embodiments, the fan units 114*a-b* can be configured to maintain a negative pressure relative to the external environment, e.g., a negative pressure less than or equal to −1 Pa, −2 Pa, −3 Pa, −4 Pa, −4.5 Pa, −5 Pa, −5.5 Pa, −6 Pa, −6.5 Pa, −7 Pa, −8 Pa, −9 Pa, −10 Pa, −15 Pa, −20 Pa, or −25 Pa. This provides a negative pressure seal that allows external air in through the gaps 112, but maintains the exhaled air within the breathing chamber such that the exhaled air does not enter the external environment.

The device 100 can also include components that sanitize (e.g., sterilize) the air entering and/or exiting the breathing chamber 108 to protect the user from infectious agents in the external environment and/or protect others from infectious agents exhaled by the user, respectively. In some embodiments, the device 100 is configured to remove and/or inactivate at least 75%, 80%, 90%, 95%, 99%, 99.5%, 99.9%, 99.99%, or 99.999% of the infectious agents entering and/or exiting the breathing chamber 108. The sanitization mechanisms of the device 100 can be configured in many different ways. For example, the arms 110*a-b* can each include one or more filters 116*a-b* configured to obstruct pathogens or other particulates from entering the breathing chamber 108. The device 100 can further include a source control mechanism (not shown) configured to obstruct and/or inactivate pathogens exiting the breathing chamber 108. Various embodiments of source control mechanisms and other sanitization mechanisms are described in greater detail below.

The device 100 can include additional functional components. For example, the device 100 can include components for securing the device 100 to the user's body, such as a nosepiece 118 and/or neck pads 120. The nosepiece 118 and/or neck pads 120 can be adjustable to accommodate the particular user's anatomy. The device 100 can also include electronic components (not shown), such as a power source (e.g., a rechargeable or non-rechargeable battery), an interface for connection to an external power source, sensors (e.g., pressure sensors, flow sensors, breath sensors), processors, memory, controllers (e.g., for the fan units 114*a-b*, power source, sensors, and/or other components of the device 100), communication devices (e.g., for wired and/or wireless communication with other devices), and the like. The electronic components can be located on or within any suitable portion of the device 100. For example, some or all of the electronic components can be housed within one or both of the arms 110*a-b*.

In some embodiments, the device 100 is a lightweight, portable device that can be worn for extended period of time with little or no user discomfort. For example, the total weight of the device 100 can be less than or equal to 500 g, 400 g, 300 g, 200 g, or 100 g. The device 100 can be configured to operate continuously for at least 1 hour, 2 hours, 3 hours, 4 hours, 5 hours, 6 hours, 7 hours, 8 hours, 9 hours, or 10 hours without recharging.

The above description of the device 100 is provided merely for illustrative purposes and is not intended to be limiting. For example, in some embodiments, one or more components of the device 100 may be omitted. Additionally, the device 100 may be modified to include additional elements not shown in FIGS. 1A-1E, such as features of any of the other respiratory devices and/or source control mechanisms described herein. Additionally, the present technology may be implemented in many different types of respirator devices and is not limited to the device 100 illustrated in FIGS. 1A-1E. The features of the device 100 may be combined with or otherwise incorporated into any of the other respirator devices described herein.

C. Selected Embodiments of Source Control Mechanisms

In some embodiments, the present technology provides respirator devices including a source control mechanism for sanitizing (e.g., sterilizing) air exhaled by a user. The term "source control mask" or grammatical variations thereof can refer to a respirator device (e.g., a face mask) configured for the sanitization and/or sterilization of exhaled air before discharging into the atmosphere. Sanitization can be formed using any suitable technique known to those of skill in the art, and can include any of the following: filtering, capturing, or trapping infectious agents or substances containing infectious agents (e.g., droplets, skin cells); killing or inactivating infectious agents; reducing the infectivity of infectious agents; and so on. Sanitization can encompass passive sanitization mechanisms (e.g., mechanical filtration based on physical size) as well as active sanitization mechanisms (e.g., ozone, electric discharge, electrostatic attraction, electrostatic precipitation, magnetic attraction, chemical inactivation, temperature inactivation). As described herein, sanitization of an air flow (e.g., exhaled and/or inhaled air) may refer to eradicating, inactivating, killing, filtering, and/or removing at least 80%, 90%, 95%, 99%, 99.5%, 99.9%, 99.99%, 99.999%, or 100% of infectious agents in the air flow. The sanitization techniques herein are applicable to many different types of infectious agents, including viruses (e.g., severe acute respiratory syndrome coronavirus 2 (SARS-CoV-2)), fungi, bacteria, and the like.

Figure 2A:
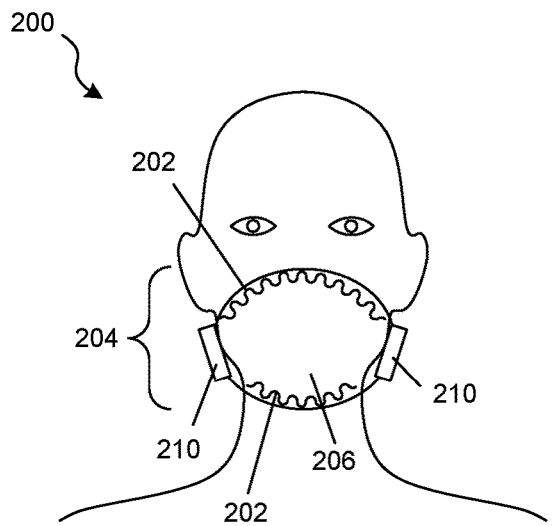
FIG. 2A is a partially schematic front view of respirator device including a source control mechanism configured in accordance with embodiments of the present technology.
Figure 2B:
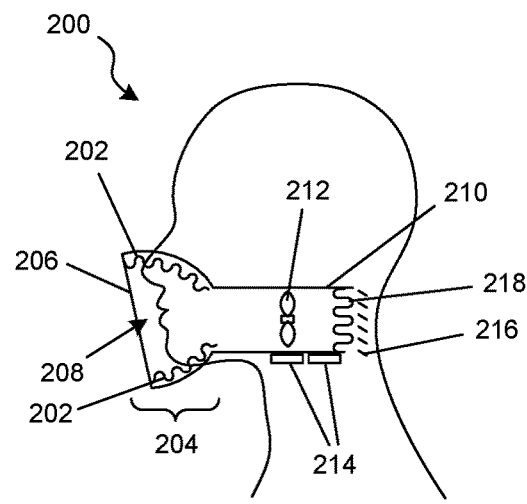
FIG. 2B is a partial cut-away side view of the respirator device of FIG. 2A.
Figure 2C:
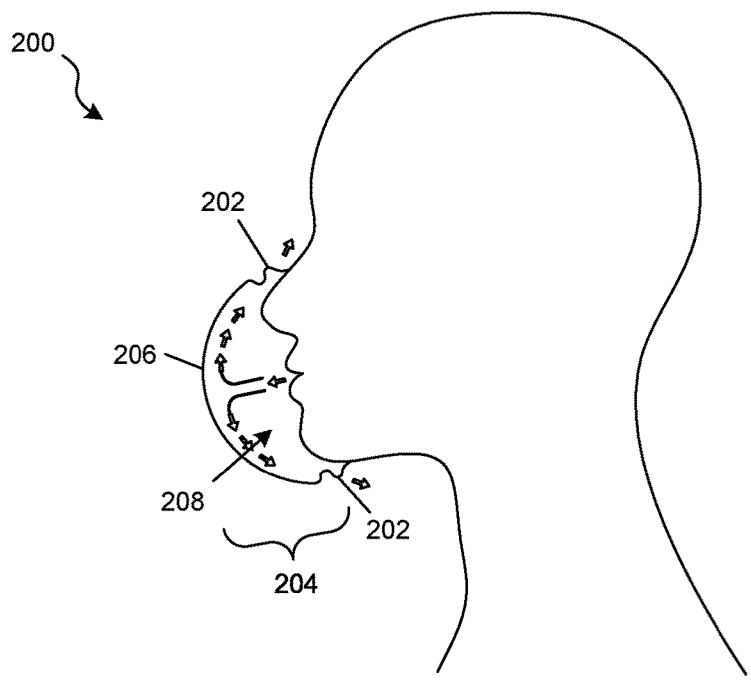
FIG. 2C is a cut-away side view of a portion of the respirator device of FIG. 2A illustrating an air flow path in accordance with embodiments of the present technology.

FIGS. 2A-2C illustrate a respirator device 200 ("device 200") including a source control mechanism 202 configured in accordance with embodiments of the present technology. More specifically, FIG. 2A is a partially schematic front view of the device 200, and FIG. 2B is a partial cut-away side view of the device 200, and FIG. 2C is a cut-away side view of a portion of the device 200 illustrating an air flow path in accordance with embodiments of the present technology.

The device 200 can be generally similar to the device 100 of FIGS. 1A-1E. For example, the device 200 includes a mask section 204 including a shield 206 configured to at least partially cover a face of a user (e.g., the user's mouth and nose). The mask section 204 can define a breathing chamber 208 between the shield 206 and the user's face, such that the user exhales air into and inhales air from the breathing chamber 208. The device 200 can include a pair of hollow elongated arms 210 coupled to the sides of the mask section 204, each arm including a respective fan unit 212, power sources 214, louver 216, and filter 218.

The source control mechanism 202 can be a flexible member (e.g., a skirt or strip of material) that extends partially or completely around the peripheral portions of the mask section 204 to seal the mask section 204 against the user's face. The source control mechanism 202 can be an attachment that may be removably coupled to the mask section 204, as discussed in greater detail below. Alternatively, the source control mechanism 202 can be permanently affixed and/or integrally formed with the mask section 204. The source control mechanism 202 can be temporarily or permanently attached to the mask section 204 using an interference fit, adhesives, bonding, fasteners, or any other suitable attachment technique.

In the illustrated embodiment, the source control mechanism 202 extends along the upper and lower edges of the shield 206, and bridges the gap between the shield 206 and the user's face (FIG. 2C). In other embodiments, however, the source control mechanism 202 can extend only along the upper edge of the shield 206, only along the lower edge of the shield 206, or any other suitable configuration. Optionally, the portions of the source control mechanism 202 that contact the user's face can be made of a soft, dermatologically-friendly, and/or non-porous material.

In some embodiments, the fan units 212 are configured to create a controlled air flow path in which air from the external environment enters the breathing chamber 208 via the arms 210, and exits the breathing chamber 208 through the source control mechanism 202. The fan units 212 can draw air into the breathing chamber 208 at a sufficiently high inflow rate such that the pressure level within the breathing chamber 208 is higher than the pressure of the external environment. For example, the air inflow rate can be at least 10 L/min, 20 L/min, 30 L/min, 40 L/min, 50 L/min, 60 L/min, 70 L/min, 80 L/min, 90 L/min, 100 L/min, 125 L/min, 150 L/min, 175 L/min, 200 L/min, 225 L/min, 250 L/min, 275 L/min, or 300 L/min. The pressure level relative to the external environment can be greater than or equal to 1 Pa, 2 Pa, 3 Pa, 4 Pa, 5 Pa, 6 Pa, 7 Pa, 8 Pa, 9 Pa, 10 Pa, 15 Pa, 20 Pa, 25 Pa, 30 Pa, 35 Pa, or 40 Pa. In some embodiments, the fan units 114a-b are configured to maintain a positive pressure relative to the external environment within a range from 5 Pa to 10 Pa during normal operation (e.g., while the user is exhaling at a normal rate), and within a range from 20 Pa to 30 Pa while the user is exhaling at a higher than normal rate (e.g., due to coughing, sneezing, heavy breathing, etc.). In some embodiments, the air flow through the breathing chamber 208 can be unidirectional or substantially unidirectional in that most or all of the air inflow enters through the arms 210, and most or all of the air outflow exits through the source control mechanism 202. For example, at least 50%, 75%, 80%, 90%, 95%, 99%, 99.5%, 99.9%, 99.99%, or 99.999% of the air entering the breathing chamber 208 can enter via the arms 210, and/or at least 50%, 75%, 80%, 90%, 95%, 99%, 99.5%, 99.9%, 99.99%, or 99.999% of the air exiting the breathing chamber 208 can exit via the source control mechanism 202.

The filters 218 and source control mechanism 202 can be configured to sanitize air entering and exiting the breathing chamber 208, respectively. The filters 218 and source control mechanism 202 can each independently be or include a sanitization mechanism configured to eradicate, inactivate, trap, filter, or otherwise reduce or prevent infectious agent(s) exhaled by the user from entering the external environment. As discussed above, the sanitization mechanism can be a passive mechanism, an active mechanism, or can include both passive and active mechanisms. Examples of sanitization mechanisms suitable for use in the filters 218 and/or source control mechanism 202 include, but are not limited to, filters, fibers (e.g., nanofibers), electrostatic, ultraviolet, chemical, temperature, ozone, magnetic, ionizing, ionizing-magnetic, and/or ionizing-electrostatic sanitization mechanisms.

In some embodiments, the primary function of the filters 218 is to produce high quality clean breathable air, while the primary function of the source control mechanism 202 is to produce air which has little or no viable infectious material (e.g., at least 80%, 90%, 95%, 99%, 99.5%, 99.9%, 99.99%, 99.999%, or 100% eradicated and/or inactivated). The source control mechanism 202 may not need to produce high quality clean breathable air, or at least not to the same degree of quality and/or cleanliness as the filters 218. For example, the air that exits to the atmosphere from the source control mechanism 202 may be non-toxic, but may not need to be 100% clean (e.g., may have droplets, but little or no viable pathogens). Accordingly, the filters 218 and source control mechanism 202 can have different sanitizing capabilities and/or use different sanitizing mechanisms. For example, in embodiments where the filters 218 are inlet filters and the source control mechanism 202 includes one or more outlet filters, the inlet filters and outlet filters can be different filter types (e.g., different pore sizes, filter materials, etc.). In some embodiments, the outlet filters have a larger pore size than the inlet filters, e.g., since pathogens exhaled by the user may generally be contained within aerosolized droplets having a relatively large size, compared to particulate pathogens that may be found in the external atmosphere. Additionally, the source control mechanism 202 may be more aggressive in how it treats and sanitizes the air. In other embodiments, however, the filters 218 and source control mechanism 202 can have the same sanitizing capabilities and/or use the same sanitizing mechanisms.

FIGS. 3A-3D illustrate various source control mechanisms configured in accordance with embodiments of the present technology. The features of the source control mechanisms can be incorporated into any of the respirator devices and source control mechanisms described herein (e.g., device 200 of FIGS. 2A-2C).

Figure 3A:
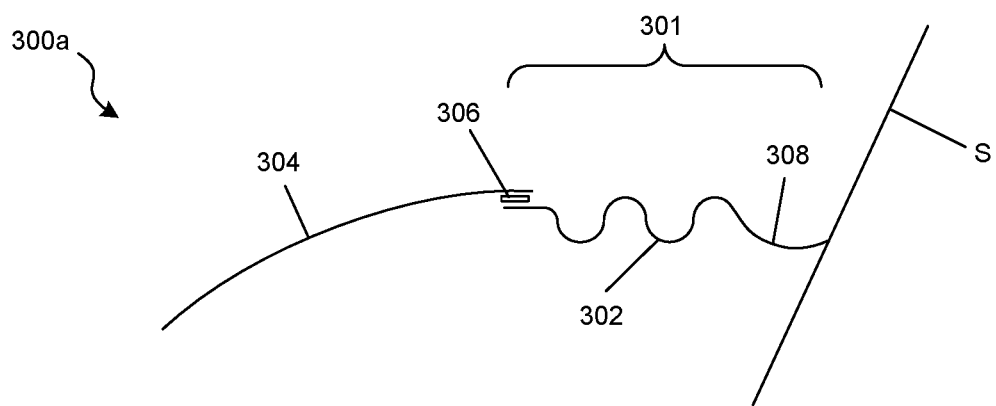
FIG. 3A is a partially schematic illustration of a portion of a respirator device including a source control mechanism with a filter section configured in accordance with embodiments of the present technology.

FIG. 3A is a partially schematic illustration of a portion of respirator device 300a ("device 300a") including a source control mechanism 301 with a filter section 302. The source control mechanism 301 can be a skirt, strip, or other flexible member configured to create a seal between a mask section 304 of the device 300a and the user's skin S. The source control mechanism 301 can be removably or fixedly coupled to the mask section 304 via an attachment element 306 (e.g., a seal, adhesive, bonding agent, fastener, etc.). The attachment element 306 can provide an air-tight seal between the source control mechanism 301 and the mask section 304. Optionally, the portion of the source control mechanism 301 that contacts the user's skin S includes a dermatological skin contact strip 308 or other biocompatible material so that the material of the filter section 302 does not contact the skin S.

The filter section 302 can be made of any suitable material with filtering and/or barrier capabilities, such as porous and/or fiber-based materials (e.g., nanofibers). The filter section 302 can be configured to filter matter that is likely to contain infectious material (e.g., droplets, skin cells, etc.) and/or can be configured to filter the infectious material itself (e.g., viruses, bacteria, fungi, etc.). For example, the filter section 302 can be configured to filter mucosalivary droplets, droplet nuclei, and/or skin cells etc. Filtration may be performed by sieving, impaction on the filter fibers, diffusion onto the filter fibers, electrostatic attraction, and/or magnetic attraction onto the filter fibers, or combinations thereof.

Figure 3B:
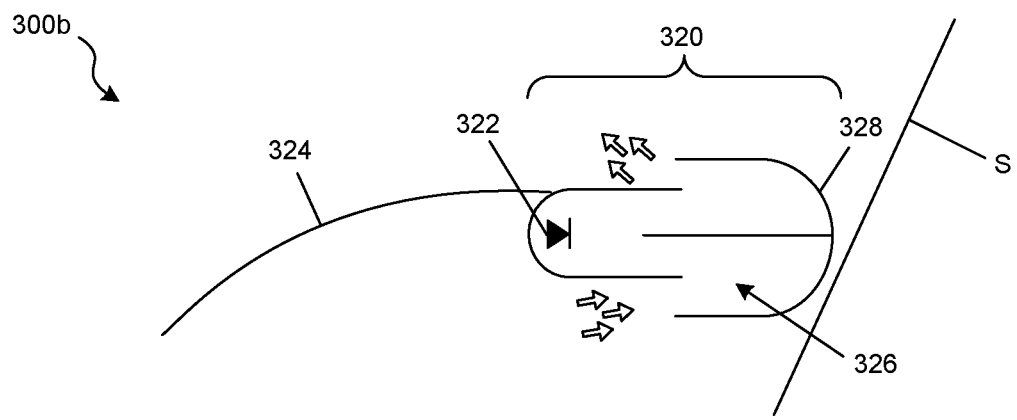
FIG. 3B is a partially schematic illustration of a portion of a respirator device including a source control mechanism with an ultraviolet light source configured in accordance with embodiments of the present technology.

FIG. 3B is a partially schematic illustration of a portion of a respirator device 300b ("device 300b") including a source control mechanism 320 with an ultraviolet light source 322 (e.g., an ultraviolet-emitting diode). The source control mechanism 320 extends between a mask section 324 of the device 300b and the user's skin S to create a seal therebetween. In the illustrated embodiment, the source control mechanism 320 includes a channel 326 for air exiting the mask section 324. The ultraviolet light source can be positioned within or otherwise operably coupled to the channel 326 so that the air passing through the channel 326 is exposed to and sanitized (e.g., sterilized) by the ultraviolet light. The ultraviolet light source 322 can be positioned in a manner so that the emitted ultraviolet light is not directed towards the user's face or eyes. Optionally, the source control mechanism 320 can include a collector 328 to prevent the ultraviolet light from reaching the user's skin S.

Figure 3C:
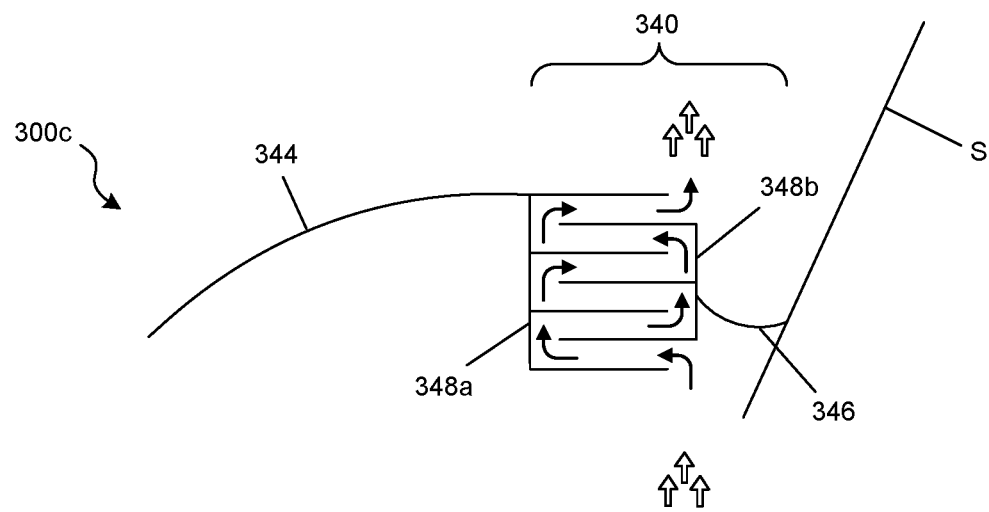
FIG. 3C is a partially schematic illustration of a portion of a respirator device including a source control mechanism with an electrostatic precipitator configured in accordance with embodiments of the present technology.

FIG. 3C is a partially schematic illustration of a portion of a respirator device 300c ("device 300c") including a source control mechanism 340 with an electrostatic precipitator 342. The source control mechanism 340 is positioned between a mask section 344 of the device 300b and the user's skin S, with an optional sealing element 346 connecting the electrostatic precipitator 342 to the skin S. The electrostatic precipitator 342 can include a positively-charged portion or side 348a, a negatively-charged portion or side 348b, and a channel 350 between the positive and negative sides 348a-b. The channel 350 can have a generally serpentine and/or zig-zag shape so that air passing through the channel 350 is sequentially and alternatingly exposed to the positive and negative sides 348a-b. Accordingly, infectious material in the air may be ionized and captured by the electrostatic precipitator 342.

Figure 3D:
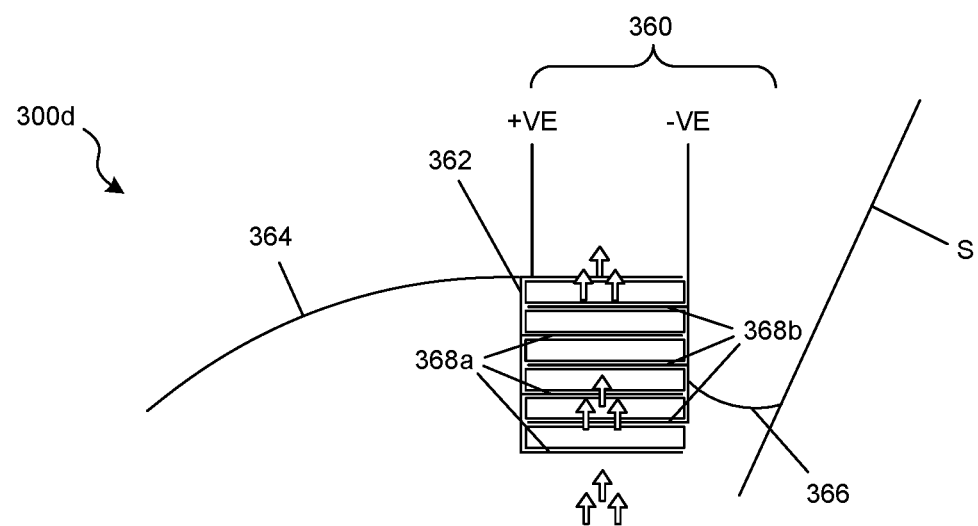
FIG. 3D is a partially schematic illustration of a portion of a respirator device including a source control mechanism with a filter assembly configured in accordance with embodiments of the present technology.

FIG. 3D is a partially schematic illustration of a portion of a respirator device 300d ("device 300d") including a source control mechanism 360 with a filter assembly 362. The source control mechanism 360 is positioned between a mask section 364 of the device 300d and the user's skin S, with an optional sealing element 366 connecting the filter assembly 362 to the skin S. The filter assembly 362 can include a plurality of first layers 368a and a plurality of second layers 368b interleaved with each other in an alternating arrangement. The first and second layers 368a-b can each be or include any suitable filtering material, such as fiber layers, porous structures, membranes, sheets, etc. Although FIG. 3D depicts the filter assembly 362 as including four first layers 368a and three second layers 368b, in other embodiments, the filter assembly 362 can include a different number of first and/or second layers 368a-b.

In some embodiments, the filter assembly 362 uses electrostatic attraction to sanitize air exiting the device 300d. For example, the electrostatic filter assembly 362 can be electrically coupled to an external power source (not shown) that provides a positive voltage +VE to the first layers 368a and a negative voltage −VE to the second layers 368b. Accordingly, the first layers 368a can be positively charged and the second layers 368b can be negatively charged. The first and second layers 368a-b can be electrically insulated from each other by an insulating material 370 positioned in the spaces between the first and second layers 368a-b. The insulating material 370 can be porous or otherwise sufficiently permeable so that air flowing out of the device 300d can pass through the filter assembly 362 and into the external environment. As air flows through the filter assembly 362, infectious material in the air (e.g., particulates) can be attracted to and captured by either the positively-charged first layers 368a or the negatively-charged second layers 368b.

Figure 4A:
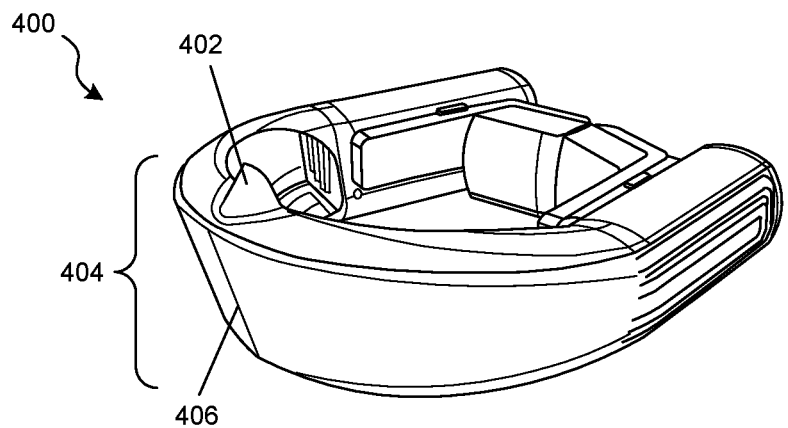
FIG. 4A is a front perspective view of a respirator device with a source control attachment configured in accordance with embodiments of the present technology.
Figure 4B:
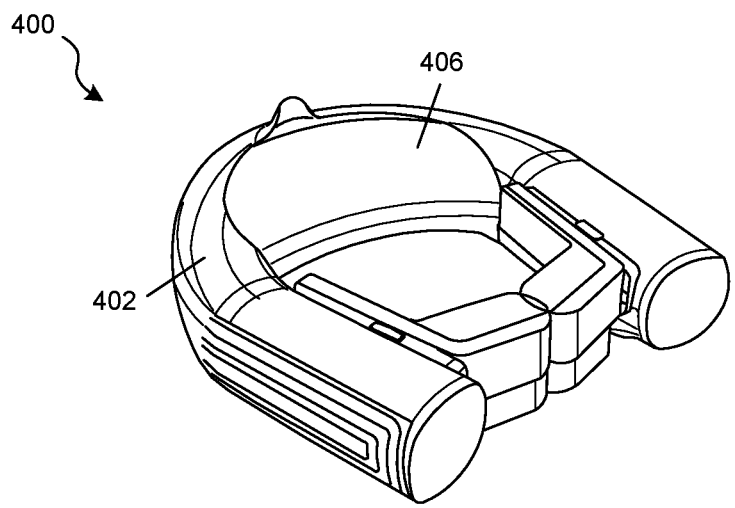
FIG. 4B is a back perspective view of the respirator device of FIG. 4A.
Figure 4C:
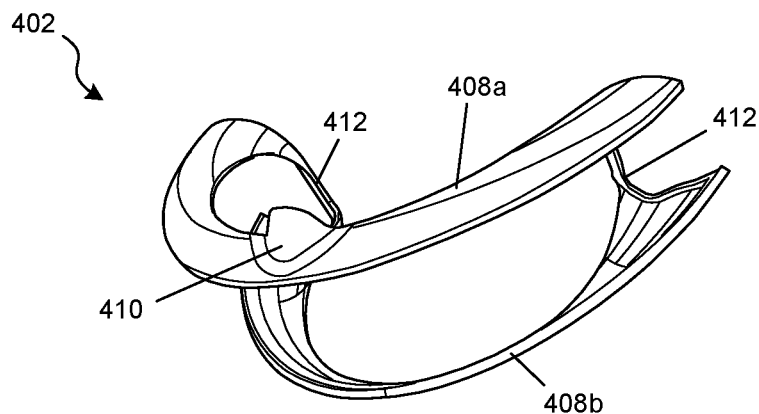
FIG. 4C is a front perspective view of the source control attachment of FIG. 4A.

FIGS. 4A-4C illustrate a respirator device 400 ("device 400") with a source control attachment 402 configured in accordance with embodiments of the present technology. More specifically, FIGS. 4A and 4B are perspective views of the device 400 and FIG. 4C is a perspective view of the source control attachment 402 when separated from the device 400. The device 400 can be an existing respirator device that does not already include source control functionality, or can be a device where augmentation of existing source control functionality is desired. In some embodiments, the device 400 is flow respirator or flow mask device, such as a non-seal continuous flow respirator (e.g., an $\overline{\text{Ao}}$ air Atmōs respirator similar to the device 100 of FIGS. 1A-1E), a powered air-purifying respirator (PAPR), or another positive pressure respirator device.

The source control attachment 402 (also referred to herein as a "source control skirt" (SCS)) can be coupled to the device 400 in order to provide the device 400 with source control functionality and/or augment existing source control functionality. The source control attachment 402 can be a source control mechanism having features identical or generally similar to the source control mechanisms of FIGS. 2A-3D. As shown in FIGS. 4A and 4B, the source control attachment 402 can be fastened partially or entirely around the perimeter of a mask section 404 and shield 406 of the device 400 (e.g., by interference fit). Accordingly, air flowing out from the mask section 404 via gaps between the mask section 404 and the user's face passes through and is sanitized by the source control attachment 402, as previously described. In some embodiments, the operating parameters of the device 400 can be adjusted to account for the presence of the source control attachment 402. For example, the device 400 can include a firmware mode that produces a higher peak internal pressure during exhalation when the source control attachment 402 is connected to the device 400.

The source control attachment 402 can have a geometry configured to conform to the corresponding geometry of the device 400. For example, as shown in FIG. 4C, the source control attachment 402 can include an upper portion 408a and a lower portion 408b. The upper portion 408a can be shaped to connect the upper edge of the mask section 404 to the user's face, and the lower portion 408b can be shaped to connect the lower edge of the mask section 404 to the user's face. Optionally, the upper portion 408a can optionally include a nosepiece 410 configured to seal against the user's nose. In some embodiments, the upper and lower portions 408a-b are coupled to each other by connecting elements 412 so that the source control attachment 402 is a single, unitary component. In other embodiments, the connecting elements 412 may be omitted, such that the upper and lower portions 408a-b are separate components that are individually fastened to the device 400.

The upper and lower portions 408a-b can each have an elongated, generally curved shape to match the corresponding shape of the mask section 404. The upper and lower portions 408a-b can be sufficiently wide so that any gap between the mask section 404 and the user's face is completely covered by the source control attachment 402. For example, the upper and lower portions 408a-b can each independently have a width (e.g., a maximum, minimum, or average width) of at least 0.25 cm, 0.5 cm, 0.75 cm, 1 cm, 1.25 cm, 1.5 cm, 2 cm, 2.5 cm, 3 cm, 3.5 cm, 4 cm, 4.5 cm, or 5 cm. The upper and lower portions 408a-b can each be or include a sanitization mechanism (e.g., one or more filters, an ultraviolet light source, an electrostatic precipitator), as previously described with respect to FIGS. 2A-3D. Accordingly, air passing through the upper and/or lower portions 408a-b can be sanitized (e.g., sterilized) before entering the external environment.

Figure 5A:
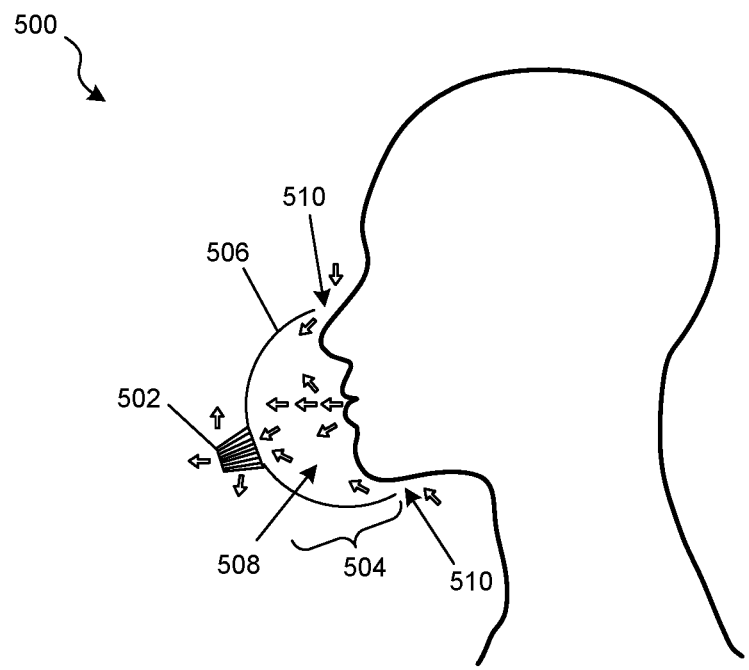
FIGS. 5A and 5B are partially schematic cut-away views of a respirator device including a source control mechanism configured in accordance with embodiments of the present technology.
Figure 5B:
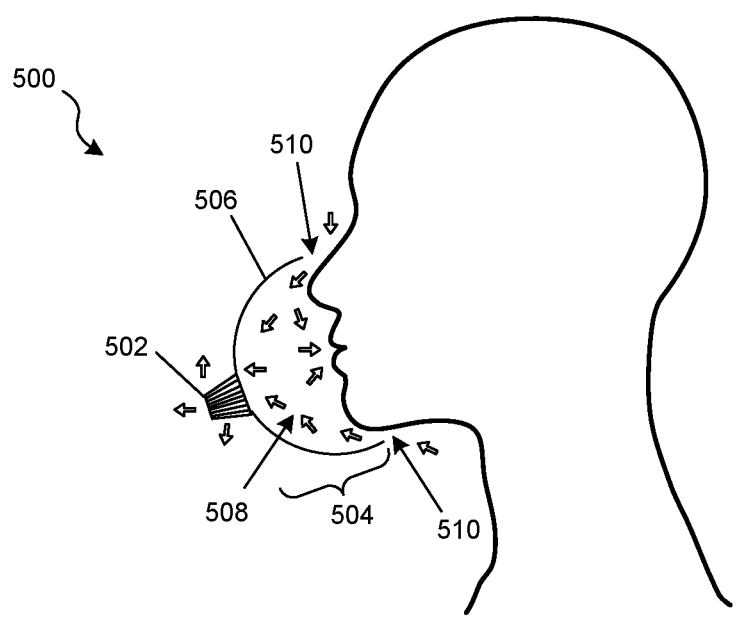

FIGS. 5A and 5B are partially schematic cut-away views of a respirator device 500 ("device 500") including a source control mechanism 502 configured in accordance with embodiments of the present technology. The respirator device 500 includes a mask section or face mask 504 including a shield 506 configured to at least partially cover a face of a user (e.g., the mouth and nose). The mask section 504 can define a breathing chamber 508 between shield 506 and the user's face, such that the user exhales air into (FIG. 5A) and inhales air from (FIG. 5B) the breathing chamber 508.

The source control mechanism 502 is coupled to an external surface of the shield 506 and is in fluid communication with the breathing chamber 508. For example, the source control mechanism can include one or more tubes, channels, lumens, passageways, etc. permitting air outflow from the breathing chamber 508 and into the external environment. The source control mechanism 502 can include at least one fan unit (not shown) configured to draw air out of the breathing chamber 508. External air can enter the breathing chamber 508 via one or more engineered gaps 510 between the shield 506 and the user's face (e.g., in an approximately even radial flow). Accordingly, the fan unit can create a controlled air flow path in which air from the external environment continuously enters the breathing chamber 508 via the gaps 510, and continuously exits the breathing chamber 508 via the source control mechanism 502. Although FIGS. 5A and 5B illustrate two gaps 510 at the upper and lower edges of the mask section 504, in other embodiments the device 500 can include a different number of gaps 510 and/or the gaps 510 can be at different locations relative to the mask section 504.

The source control mechanism 502 can include a sanitization mechanism, such as one or more filters or filter systems. The sanitization mechanism can eradicate, inactivate, trap, filter, or otherwise reduce or prevent infectious agent(s) exhaled by the user from entering the external environment. As discussed above, the sanitization mechanism can be a passive mechanism, an active mechanism, or can include both passive and active mechanisms. Examples of sanitization mechanisms suitable for use in the source control mechanism 502 include, but are not limited to, filters, fibers (e.g., microfibers, nanofibers), electrostatic, ultraviolet, chemical, temperature, ozone, ionizing, ionizing-magnetic, and/or ionizing-electrostatic sanitization mechanisms.

The fan unit can draw air from the breathing chamber 508 at a sufficiently high outflow or extraction rate such that the pressure level within the breathing chamber 508 is lower than the pressure of the external environment. For example, the pressure level relative to the external environment can be less than or equal to −1 Pa, −2 Pa, −3 Pa, −4 Pa, −4.5 Pa, −5 Pa, −5.5 Pa, −6 Pa, −6.5 Pa, −7 Pa, −8 Pa, −9 Pa, −10 Pa, −15 Pa, −20 Pa, or −25 Pa. Accordingly, little or no air exits the breathing chamber 508 through the gaps 510, and the source control mechanism 502 can be the only air outflow path from the breathing chamber 508. For example, at least 50%, 75%, 80%, 90%, 95%, 99%, 99.5%, 99.9%, 99.99%, or 99.999% of the air in the breathing chamber 508 can exit via the source control mechanism 502. Accordingly, the air flow path can be substantially or completely unidirectional, with atmospheric air continually entering the breathing chamber 508 via the gaps 510 and preventing infected air within the breathing chamber 508 from entering the atmosphere without sanitization.

The extraction rate of the fan unit may be greater than the exhalation rate of the user such that the user's breathing does not substantially pressurize the breathing chamber 508 and/or disrupt the air flow path. For example, the extraction rate can be higher than the user's exhalation rate during any of the following: normal activity, exercise, talking, coughing, or sneezing. In some embodiments, the extraction rate can be greater than or equal to 10 L/min, 20 L/min, 30 L/min, 40 L/min, 50 L/min, 60 L/min, 70 L/min, 80 L/min, 90 L/min, 100 L/min, 125 L/min, 150 L/min, 175 L/min, 200 L/min, 225 L/min, 250 L/min, 275 L/min, or 300 L/min. The device 500 can include one or more sensors (e.g., pressure sensors; not shown) to monitor the relative pressure between the breathing chamber 508 and the surrounding atmosphere to ensure the appropriate extraction rate is maintained and that the device 500 is in compliance. Optionally, the device 500 can adjust the extraction rate of the fan unit based on detected pressure (e.g., by changing the rotation speed of the fan via a suitable controller). For example, if the pressure increases above a threshold level, the device 500 can increase the extraction rate until the pressure drops back below the threshold.

FIGS. 6A-6D are partially schematic illustrations of various mounting locations for source control mechanisms in accordance with embodiments of the present technology. The features of the respirator devices shown in FIGS. 6A-6D can be applied to any of the respirator devices described herein (e.g., the device 500 of FIGS. 5A and 5B).

Figure 6A:
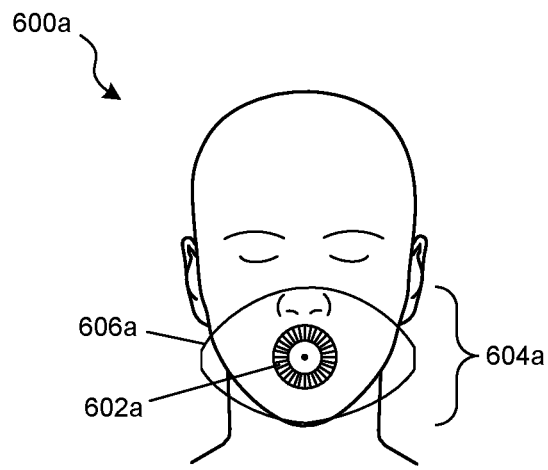
FIGS. 6A-6D are partially schematic illustrations of mounting locations for source control mechanisms in accordance with embodiments of the present technology.

FIG. 6A illustrates a respirator device 600*a* ("device 600*a*") including a single source control mechanism 602*a* (e.g., a fan extractor) mounted on the front surface of the mask section 604*a* at or near the center of the shield 606*a*. The central location of the source control mechanism 602*a* may be beneficial for producing even air flow through the device 600*a*.

Figure 6B:
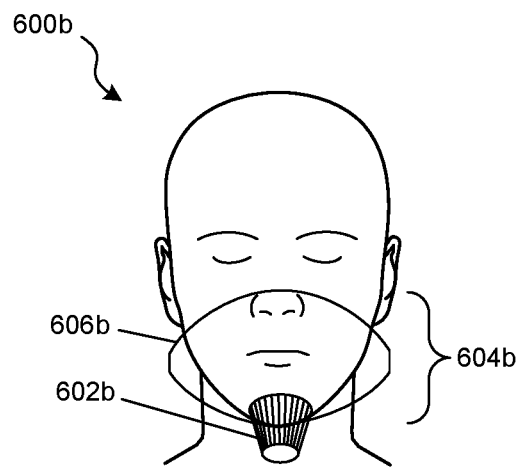

FIG. 6B illustrates a respirator device 600*b* ("device 600*b*") including a single source control mechanism 602*b* mounted on the front surface of the mask section 604*b* at or near a bottom portion of the shield 606*b*, such that the source control mechanism 602*b* is near or underneath the user's chin. In such embodiments, the air outflow from the source control mechanism 602*b* can be directed downward and away from the user's face. This approach can further reduce the likelihood of disease transmission because the air extracted from the device 600*b* can be deflected away from the faces of other individuals near the user.

Figure 6C:
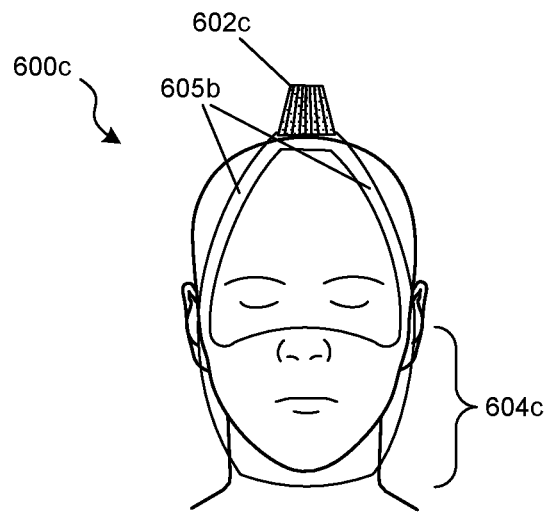

FIG. 6C illustrates a respirator device 600*c* ("device 600*c*") including a single source control mechanism 602*c* spaced apart from the mask section 604*c*. In the illustrated embodiment, the source control mechanism 602*c* is mounted on top of the user's head and is connected to the mask section 604*c* via one or more air tubes 605*c*. In other embodiments, however, the source control mechanism can be positioned at a different location, e.g., at a side of the user's head, behind the user's head, at the user's neck or chest, etc. This configuration can reduce the degree to which the device 600*c* obstructs the user's face, and can also deflect the air outflow away from the user's face and/or other individuals near the user.

Figure 6D:
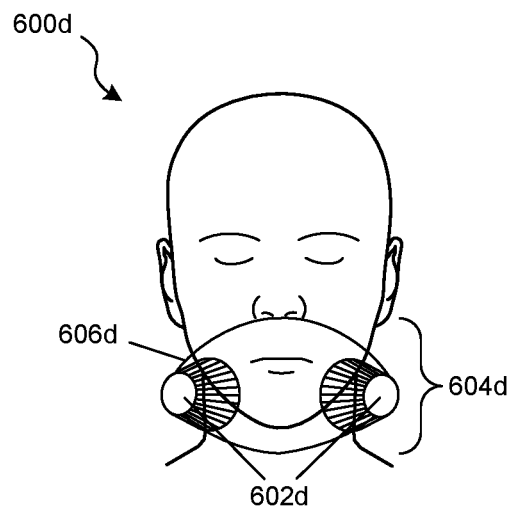

FIG. 6D illustrates a respirator device 600*d* ("device 600*d*") including two source control mechanisms 602*d*. In the illustrated embodiment, the source control mechanisms 602*d* are mounted on the front surface of the mask section 604*d* (e.g., on the shield 606*d*), and are laterally offset from the center of the mask section 604*d* so that air outflow is directed laterally outwards. The use of multiple source control mechanisms 602*d* can improve the air extraction rate and sanitization capabilities of the device 600*d*. Although FIG. 6D illustrates two source control mechanism 602*d*, in other embodiments, the device 600*d* can include three, four, five, or more source control mechanisms distributed at various locations of the device 600*d*. In some embodiments, the shield 606*d* can be designed to deflect the exhaled air back, through the source control mechanisms 602*d* with the air exiting behind the user rather than toward the user.

Figure 7A:
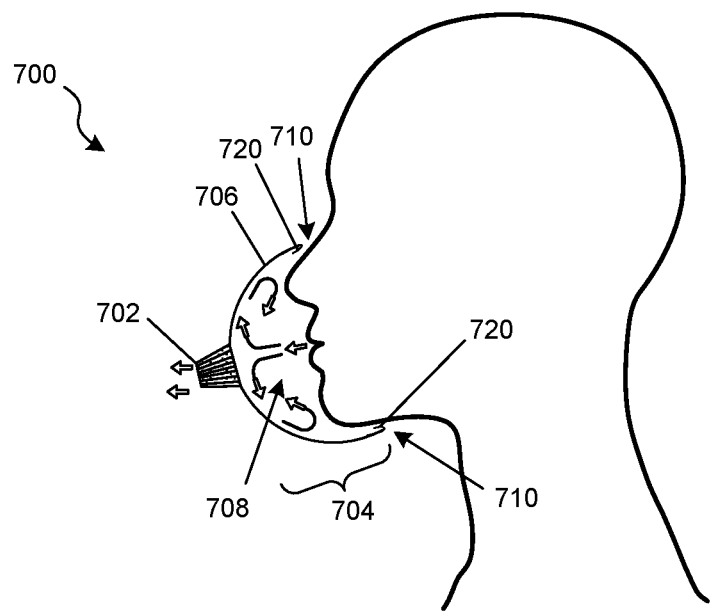
FIGS. 7A and 7B are partially schematic cut-away views of a respirator device including one or more sealing members configured in accordance with embodiments of the present technology.
Figure 7B:
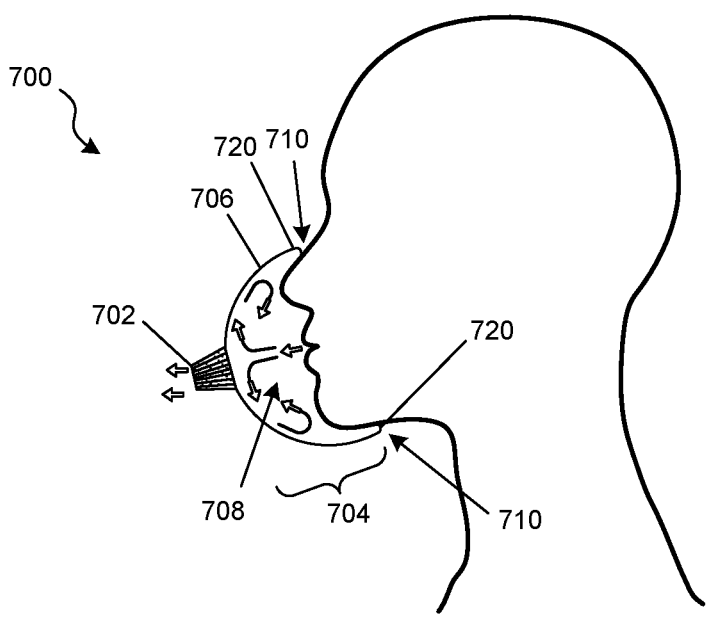

FIGS. 7A and 7B are partially schematic cut-away views of a respirator device 700 including one or more sealing members 720 configured in accordance with embodiments of the present technology. The device 700 can be generally similar to the device 500 of FIGS. 5A and 5B, except for the addition of the sealing members 720. Accordingly, like numbers are used to identify similar or identical components (e.g., source control mechanism 702 versus source control mechanism 502), and the description of the device 700 will be limited to those features that differ from the device 500 of FIGS. 5A and 5B.

The sealing members 720 are coupled to the mask section 704 at or near the gaps 710 between the shield 706 and the user's face. The sealing members 720 can be any component capable of moving between an open configuration (FIG. 7A) and a closed configuration (FIG. 7B), such as flaps, skirts, valves, etc. When the sealing members 720 are in the open configuration, external air can flow into the breathing chamber 708 via the gaps 710. When the sealing members 720 are in the closed configuration, the sealing members 720 can cover the gaps 710 and seal against the user's face to reduce or prevent air flow into the breathing chamber 708. Although FIGS. 7A and 7B illustrate two sealing members 720 at the upper and lower edges of the mask section 704, in other embodiments the number and locations of the sealing members 720 can be varied, e.g., based on the number and locations of the gaps 710.

In some embodiments, the sealing members 720 serve as "blow close" flaps that automatically close in situations where air is likely to leak from the breathing chamber 708 into the surrounding environment. For example, when the user coughs or sneezes, the amount of air being ejected into the breathing chamber 708 may be too great for the fan unit of the source control mechanism 702 to maintain the desired level of negative pressure, thus creating a risk that unsanitized air will escape via the gaps 710. Accordingly, the sealing members 720 may automatically close to form an air-tight seal between the user's face and the shield 706, thus capturing the air from the cough or sneeze, and giving the fan unit time to catch up and extract the air from the breathing chamber 708 via the source control mechanism 702. Optionally, the sealing members 720 can be made of a filtering material to sanitize any air that escapes from the breathing chamber 708 via the gaps 710.

The sealing members 720 can be configured in many different ways. For example, the sealing members 720 can be made from an elastic, flexible material, such as a polymer or elastomer. In such embodiments, the sealing members 720 can be elastically biased to the open configuration, and can be closed by an applied force sufficient to overcome the elastic bias (e.g., pressure levels within the breathing chamber 708, an actuation element that is activated to open the sealing members 720, etc.). Once the applied force is removed, the sealing members 720 can automatically return to the open configuration. Conversely, the sealing members 720 can be elastically biased to the closed configuration, and can be held open by an applied force (e.g., air inflow, an actuation element, etc.). The applied force can be removed to automatically close the sealing members 720.

As another example, the sealing members 720 may be held in the open configuration by the inrushing air, and may automatically close when the pressure in the breathing chamber 708 falls to approximately zero. As the pressure rises inside the breathing chamber 708, it may push against the sealing members 720 to exert a greater force on the seal, thus increasing its sealing effectiveness. Once the pressure in the breathing chamber 708 falls back below the threshold, the sealing members 720 can automatically return to the open configuration. Alternatively or in combination, the sealing members 720 may be operated by other mechanisms such as an electromechanical action, magnets, springs, and so on.

In some embodiments, the device 700 is configured to predict and/or detect a cough, sneeze, and/or other event likely to result in leakage of unsanitized air. For example, the device 700 can include one or more pressure sensors (not shown) that measuring the pressure in the breathing chamber 708. If the pressure goes over a predetermined threshold (e.g., −5 Pa relative to the ambient environment), the device 700 can close the sealing members 720 (e.g., via an electromechanical mechanism or other actuation mechanism). Alternatively or in combination, the device 700 may also predict an oncoming cough or sneeze by detecting a sharp intake of breath or other respiratory tell-tale signs, e.g., using a flow sensor, breath sensor, audio sensor, etc. If a cough, sneeze, and/or other such event is detected and/or predicted, the device 700 can automatically close the sealing members 720.

Figure 8A:
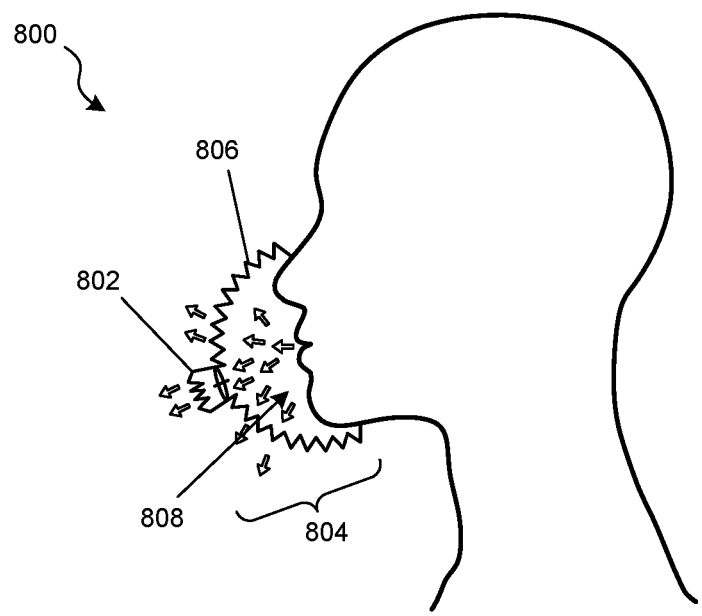
FIGS. 8A and 8B are partially schematic cut-away views of an expandable respirator device including a source control mechanism configured in accordance with embodiments of the present technology.
Figure 8B:
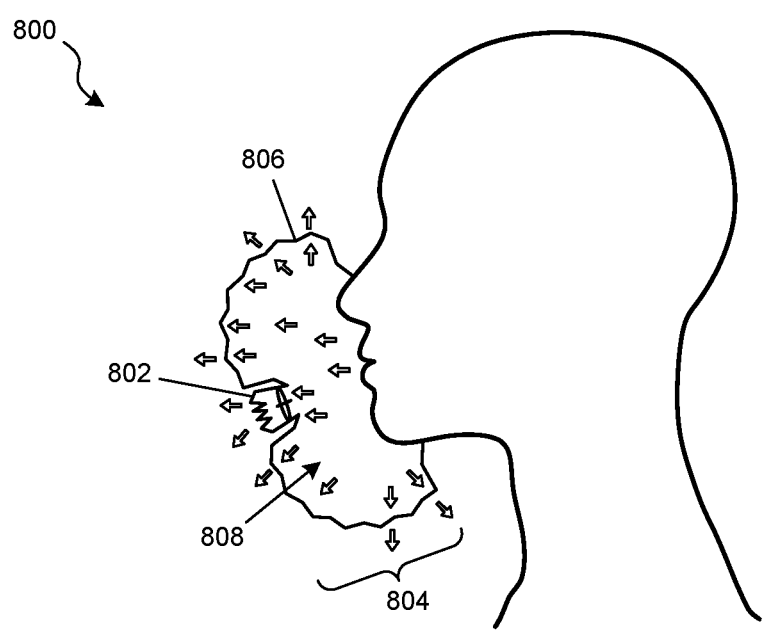

FIGS. 8A and 8B are partially schematic cut-away views of an expandable respirator device 800 ("device 800") including a source control mechanism 802 configured in accordance with embodiments of the present technology. The device 800 includes a mask section 804 made of or including an expandable material 806, such as a pleated, furled, folded, and/or elastic material. The mask section 804 can be a tight-fitting sealed mask that does not includes gaps between the edges of the mask section 804 and the user's face. As such, the expandable material 806 of the mask section 804 can be air-permeable (e.g., porous) to permit entry of external air into the breathing chamber. Optionally, the expandable material 806 can also be or include a filter material that sanitizes the incoming air.

The source control mechanism 802 can be identical or generally similar to the corresponding embodiments of FIGS. 5A-7B. For example, the source control mechanism 802 can be mounted to the mask section 804, and can include at least one fan unit configured to draw air out of the breathing chamber 808. The fan unit can draw air from the breathing chamber 808 at a sufficiently high outflow rate such that the pressure level within the breathing chamber 808 is lower than the pressure of the external environment, and the source control mechanism 802 is the primary or only air outflow path from the breathing chamber 808. The source control mechanism 802 can also include a filter or other mechanism for sanitizing the outgoing air. Accordingly, the device 800 may be used to filter both the incoming and the outgoing air. The device 800 can function as an open system in that as the user breathes, the atmospheric air is filtered by the expandable material 806 of the mask section 804. During this phase, the fan unit may continually extract the air from the breathing chamber 808, thus scrubbing the exhaled breath before the next breath is taken, and therefore reducing or avoiding re-breathing.

The mask section 804 can be configured to transform between a resting configuration (FIG. 8A) and an expanded configuration (FIG. 8B). The mask section 804 can be in the resting configuration while the user has a normal (e.g., relatively low) exhalation rate. In the resting configuration, the expandable material 806 is in an unexpanded and/or relaxed state so that the breathing chamber 808 has a relatively small volume. The mask section 804 can expand outwards and away from the user's face if the user coughs, sneezes, or otherwise exhibits a relatively high exhalation rate. The expandable material 806 can stretch, unfold, unfurl, etc. to increase the volume of the breathing chamber 808. For example, the expanded volume of the breathing chamber 808 can be at least 150%, 200%, 250%, 300%, 350%, 400%, 450%, or 500% of the resting volume. The expansion of the mask section 804 can reduce or prevent pressurization of the breathing chamber 808 that may break the seal against the user's face and allow unsanitized air to escape. The expansion can also give the fan unit time to extract the additional air from the breathing chamber 808. The expandable material 806 can be biased towards the resting configuration such that the mask section 804 automatically shrinks back to the resting volume once the pressure within the breathing chamber 808 is sufficiently low.

Figure 9A:
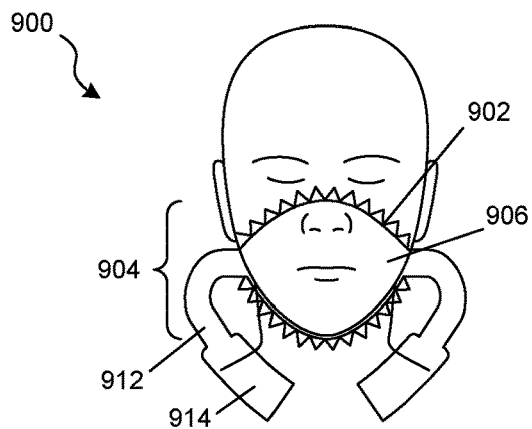
FIG. 9A is a partially schematic front view of a respirator device with expandable pleats configured in accordance with embodiments of the present technology.
Figure 9B:
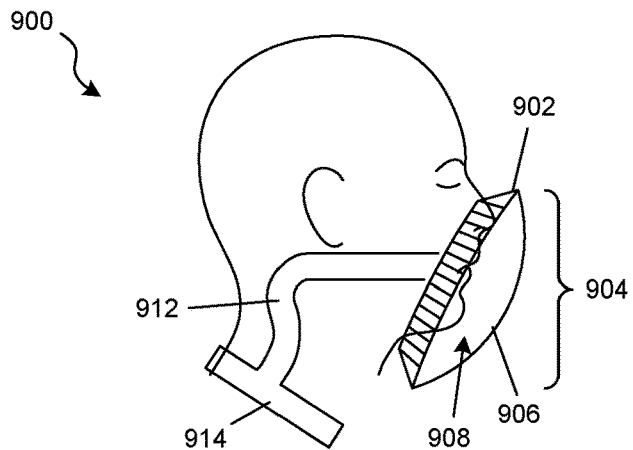
FIG. 9B is a side view of the respirator device of FIG. 9A.
Figure 9C:
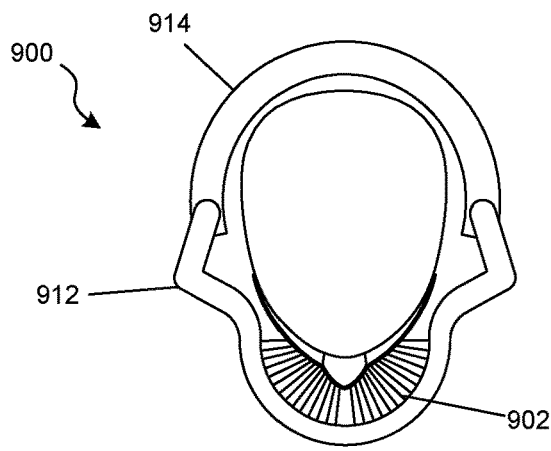
FIG. 9C is a top view of the respirator device of FIG. 9A.

FIGS. 9A-9C illustrate a respirator device 900 ("device 900") with expandable pleats 902 configured in accordance with embodiments of the present technology. The device 900 includes a mask section 904 with a shield 906 that at least partially covers the user's face and forms a breathing chamber 908 therein. The pleats 902 are coupled to the peripheral portions of the mask section 904, partially or entirely around the shield 906. For example, the pleats 902 can be located along the upper edge, lower edge, and/or lateral edges of the shield 906. The pleats 902 can be made of any suitable expandable material, such as elastic expansion fabric, a filter material, and/or elastomeric material. The pleats 902 can seal against the user's face so the there are no gaps between the edges of the mask section 904 and the user's face. As such, the pleats 902 can be air-permeable (e.g., porous) to permit entry of external air into the breathing chamber 908.

In normal operation of the device 900, as the user exhales, the air can be drawn from the breathing chamber 908 by one or more fan units (not shown) in fluid communication with the breathing chamber 908. For example, in the illustrated embodiment, the device 900 includes one or more tubes or 912 coupled to the sides of the mask section 904, and the fan units can be located within or near the tubes 912. The tubes 912 can be coupled to a filter assembly 914 spaced apart from the mask section 904, e.g., at or near the back of user's neck, or any other suitable location. Additional device components (e.g., power sources, controllers, etc.) may also be coupled to or located near the filter assembly 914. Air exiting the breathing chamber 908 can pass through the tubes 912 and the filter assembly 914 before entering the external environment. Accordingly, the filter assembly 914 can serve as a source control mechanism for the device 900 by sanitizing the outgoing air.

The fan units can draw air from the breathing chamber 908 at a sufficiently high outflow rate such that the pressure level within the breathing chamber 908 is lower than the pressure of the external environment. Thus, as the user pauses between breaths, air from the external environment can be drawn through the pleats 902 into the negative pressure breathing chamber 908, and can flush the exhaled air from the breathing chamber 908. The pleats 902 can be configured to filter or otherwise sanitize the air entering the breathing chamber 908 so that the incoming air flow is also clean. The negative pressure in the breathing chamber 908 can decrease further when the user inhales, which can further facilitate air flow from the external environment, through the pleats 902, and into the breathing chamber 908.

The pleats 902 can be configured to transform between a resting configuration (shown in FIGS. 9A-9C) and an expanded configuration (not shown) to prevent disruption of the seal against the user's face, similar to the principle of operation of the device 800 of FIGS. 8A and 8B. For example, the pleats 902 can remain in the resting configuration while the user has a normal (e.g., relatively low) exhalation rate. In the resting configuration, the pleats 902 can be in an unexpanded and/or relaxed state so that the breathing chamber 908 has a relatively small volume. If the user coughs, sneezes, or otherwise exhibits a relatively high exhalation rate, the pleats 902 can stretch, unfold, unfurl, etc. into their expanded configuration to increase the volume of the breathing chamber 908. For example, when the pleats 902 are expanded, the volume of the breathing chamber 908 can be at least 150%, 200%, 250%, 300%, 350%, 400%, 450%, or 500% of the resting volume. The expansion of the pleats 902 can reduce or prevent pressurization of the breathing chamber 908 that may break the seal against the user's face and allow unsanitized air to escape. The expansion can also give the fans time to extract the additional air from the breathing chamber 908. The pleats 902 can automatically return back to the resting configuration once the pressure within the breathing chamber 908 has lowered to normal levels.

Although various embodiments herein have been described in the context of powered respirator devices (e.g., devices including a fan unit or other mechanism for circulating air through the breathing chamber), it will be appreciated that in alternative embodiments, the source control mechanisms described herein can be used with respirator devices that do not include any powered mechanisms for driving air flow.

Figure 10A:
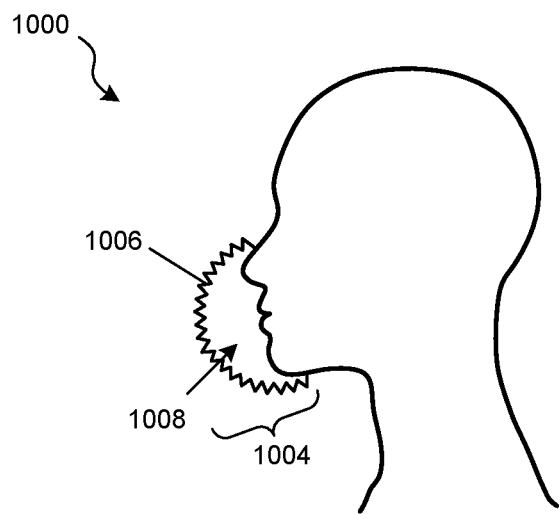
FIGS. 10A and 10B are partially schematic cut-away views of an expandable respirator device configured in accordance with embodiments of the present technology.
Figure 10B:
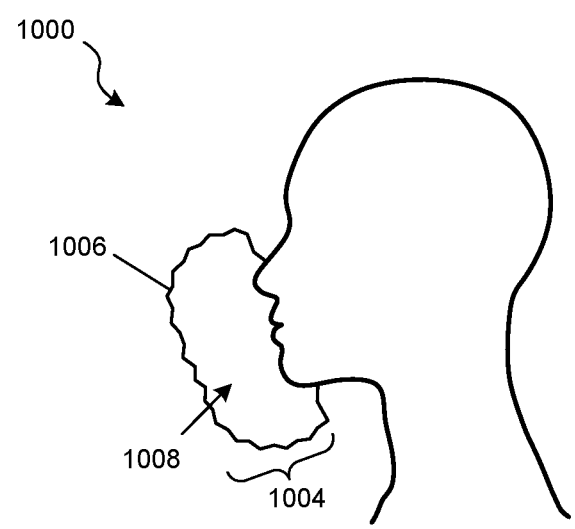

FIGS. 10A and 10B are partially schematic cut-away views of an expandable respirator device 1000 ("device 1000") configured in accordance with embodiments of the present technology. The features of the device 1000 can be generally similar to the device 800 of FIGS. 8A and 8B, except that the device 1000 does not include a fan unit or any other powered mechanism for circulating air through the device 1000. Instead, the device 1000 utilizes the user's breath to draw air into and out of the breathing chamber 1008. The device 1000 includes a mask section 1004 made of or including an expandable material 1006 (e.g., a pleated, furled, folded, and/or elastic material). The mask section 1004 can be a tight-fitting sealed mask that does not includes gaps between the edges of the mask section 1004 and the user's face. The expandable material 1006 of the mask section 1004 can be air-permeable (e.g., porous) to permit air to enter and exit the breathing chamber 1008. Optionally, the expandable material 1006 can be or include a filter material that sanitizes the incoming and outgoing air. In such embodiments, the expandable material 1006 serves as the source control mechanism for the device 1000.

The mask section 1004 can be configured to transform between a resting configuration (FIG. 10A) and an expanded configuration (FIG. 10B) to prevent unsanitized air from entering and/or exiting the breathing chamber 1008 during a cough, sneeze, or other high exhalation event. The mask section 1004 can be in the resting configuration while the user has a normal (e.g., relatively low) exhalation rate. In the resting configuration, the expandable material 1006 is in an unexpanded and/or resting state so that the breathing chamber 1008 has a relatively small volume. The mask section 1004 can expand outwards and away from the user's face if the user coughs, sneezes, or otherwise causes the breathing chamber 1008 to pressurize. The expandable material 1006 can stretch, unfold, unfurl, etc. so that the volume of the breathing chamber 1008 increases when in the expanded configuration. For example, the expanded volume of the breathing chamber 1008 can be at least 150%, 200%, 250%, 300%, 350%, 400%, 450%, or 500% of the resting configuration. The expansion of the mask section 1004 can reduce or prevent pressurization of the breathing chamber 1008 that may break the seal against the user's face and allow unsanitized air to escape. The expandable material 1006 can be biased towards the resting configuration such that the mask section 1004 automatically shrinks back to the resting volume once the pressure within the breathing chamber 1008 returns to normal.

D. Additional Respirator Device Components and Features

FIGS. 11A-14B and the following description provide various components and features that may be incorporated into any of the respirator devices described herein (e.g., any of the devices of FIGS. 1A-10B).

Figure 11A:
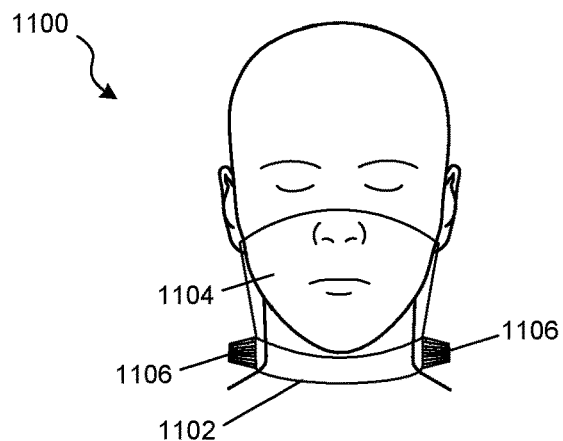
FIG. 11A is a partially schematic front view of a respirator device with a collar mount system configured in accordance with embodiments of the present technology.
Figure 11B:
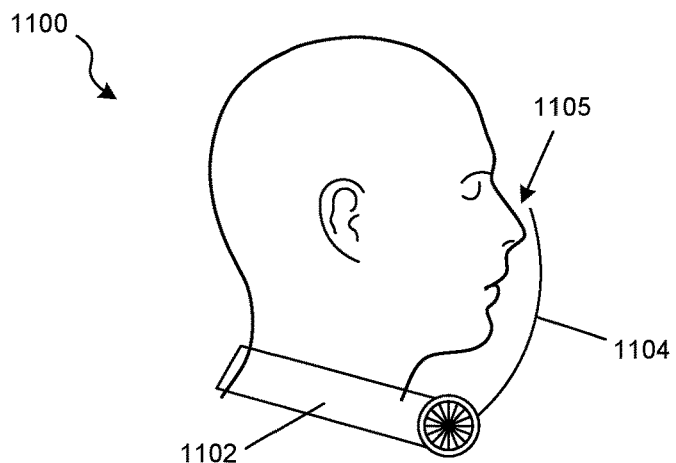
FIG. 11B is a side view of the respirator device of FIG. 11A.
Figure 11C:
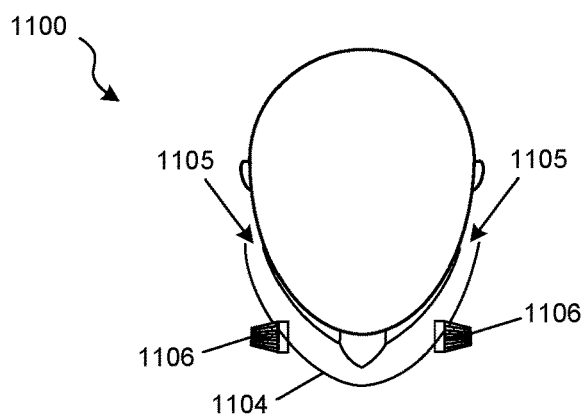
FIG. 11C is a top view of the respirator device of FIG. 11A.

FIGS. 11A-11C illustrate a respirator device 1100 ("device 1100") with a collar mount system 1102 configured in accordance with embodiments of the present technology. The collar mount system 1102 can include a collar, ring, neckpiece, etc. that is configured to fit partially or entirely around the user's neck. The size (e.g., diameter) of the collar mount system 1102 can be adjustable to accommodate different body sizes. The collar mount system 1102 can be fastened using buckles, straps, hook-and-loop fasteners, or any other suitable removable attachment device. The collar mount system 1102 can be removably or permanently attached to the lower portion of the mask section or shield 1104 of the device 1100 (e.g., via adhesives, bonding, interference fit, fasteners, etc.). Accordingly, the collar mount system 1102 can support and maintain the shield 1104 in a position covering at least a portion of the user's face (e.g., the nose and mouth). When attached to the collar mount system 1102, the shield 1104 can be separated from the user's face by one or more gaps 1105 (e.g., along the upper and/or lateral edges of the shield 1104). The gaps 1105 may be left open, or may be covered with a material (e.g., a filter or a source control mechanism). In some embodiments, the collar mount system 1102 supports the shield 1104 so it does not contact the user's face, which may reduce user discomfort, among other advantages.

Optionally, the collar mount system 1102 can be coupled to and/or include other functional components of the device 1100, such as one or more source control mechanisms 1106, sensors, power sources, and/or other electronics. For example, in the illustrated embodiment, the device 1100 includes two source control mechanisms 1106 coupled to the collar mount system 1102 (e.g., at the sides of the user's neck). In other embodiments, however, the device 1100 can include a different number of source control mechanisms 1106 and/or the source control mechanisms 1106 can be positioned at different locations on the collar mount system 1102. The source control mechanisms 1106 can be fluidly coupled to the breathing chamber of the device 1100 using tubes or other connectors, which may be incorporated into the collar mount system 1102 or can be separate from the collar mount system 1102.

Figure 12A:
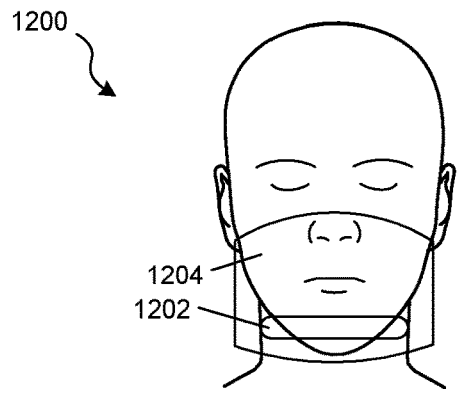
FIG. 12A is a partially schematic front view of a portion of a respirator device with a handle configured in accordance with embodiments of the present technology.
Figure 12B:
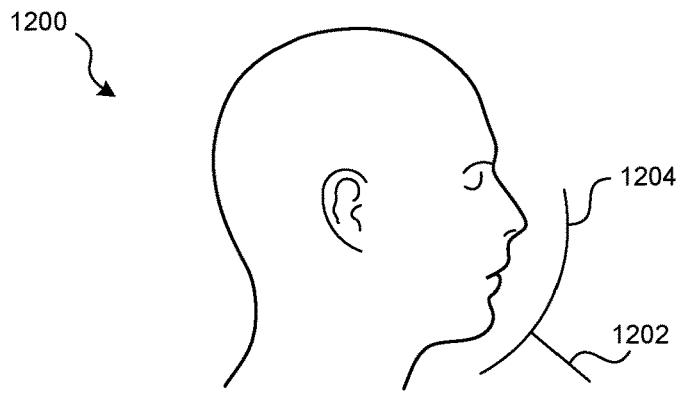
FIG. 12B is a side view of the respirator device of FIG. 12A.
Figure 12C:
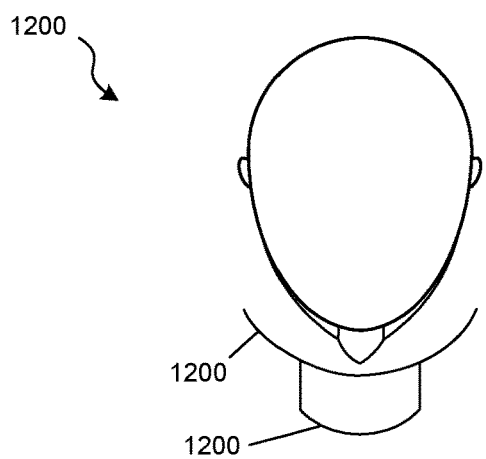
FIG. 12C is a top view of the respirator device of FIG. 12A.

FIGS. 12A-12C illustrate a respirator device 1200 ("device 1200") with a handle 1202 configured in accordance with embodiments of the present technology. In the illustrated embodiment, the handle 1202 is attached to the front surface of the mask section or shield 1204, e.g., near the bottom portion of the shield 1204. In other embodiments, the handle 1202 can be coupled to other portions of the shield 1204, e.g., near the top portion, near a peripheral portion, to an edge, etc. The handle 1202 can be used by the user or another individual to don and/or doff the device 1200. For example, the handle 1202 can be used to temporarily pull the shield away from the user's face, e.g., so the user can blow their nose, wipe their face, etc. Advantageously, the handle 1202 allows the shield 1204 to be temporarily moved away from the user's face without completely removing the device 1200 and/or unfastening other attachment elements (e.g., undoing head straps). Furthermore, the handle 1202 may allow this action to be completed without compromising the sanitary field.

Figure 13A:
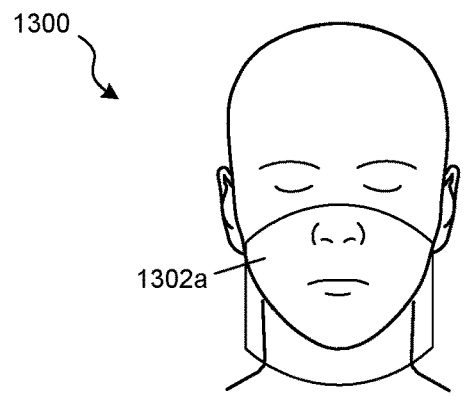
FIG. 13A is a partially schematic front view of a portion of a respirator device including multiple shields configured in accordance with embodiments of the present technology.
Figure 13B:
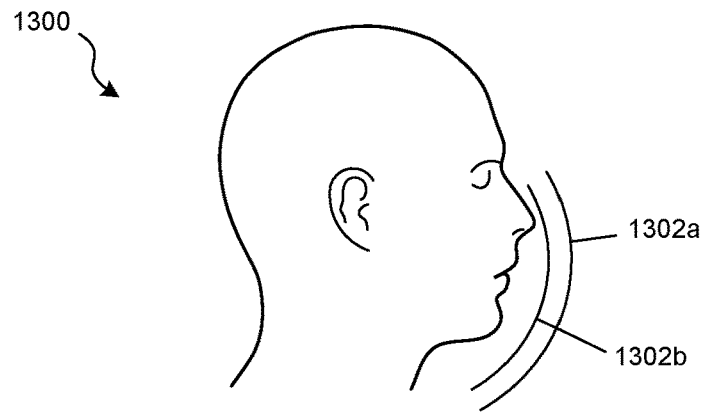
FIG. 13B is a schematic side view of the device of FIG. 13A.
Figure 13C:
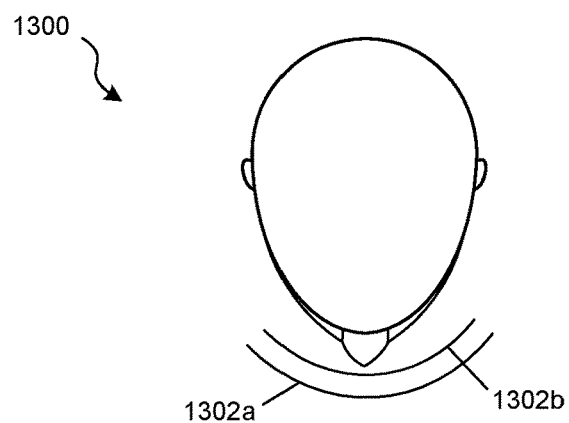
FIG. 13C is a schematic top view of the device of FIG. 13A.

FIGS. 13A-13C illustrate a respirator device 1300 ("device 1300") including multiple shields configured in accordance with embodiments of the present technology. In the illustrated embodiment, the device 1300 includes a first, outer shield 1302a and a second, inner shield 1302b. One or both of the first and second shields 1302a-b can be removable, e.g., without little or no disruption to the operation of the device 1300. For example, as the user coughs or sneezes, the second shield 1302b may become contaminated with mucus, foreign contaminates, infectious particles, and/or the like. The second shield 1302b may be removed, and, optionally, a clean replacement shield inserted in its place. During this time, the device 1300 may continue to operate without interruption as the first shield 1302a remains in place. As another example, the first shield 1302a may become contaminated when the user enters an environment with infectious and/or hazardous material in the air, and can be removed and replaced with a clean shield. The device 1300 can continue operating while the first shield 1302a is replaced since the second shield 1302b remains in place.

Figure 14A:
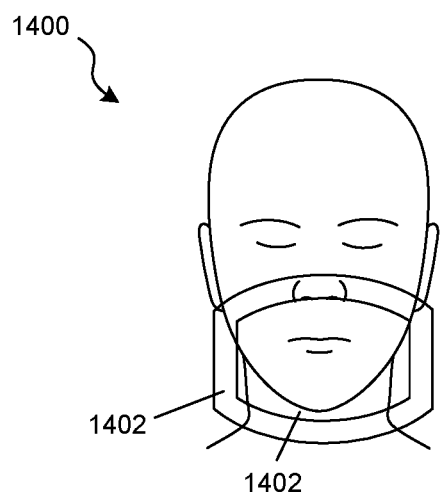
FIG. 14A is a partially schematic front view of a portion of a respirator device including a frame configured in accordance with embodiments of the present technology.
Figure 14B:
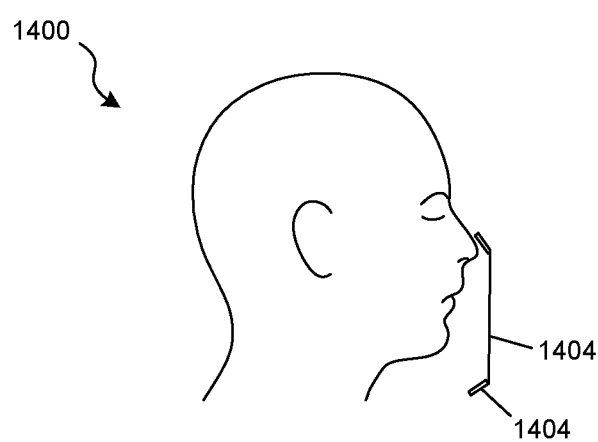
FIG. 14B is a side view of the respirator device of FIG. 14A.

FIGS. 14A and 14B illustrate a respirator device 1400 ("device 1400") including a frame 1402 configured in accordance with embodiments of the present technology. The frame 1402 can be used to support a shield 1404 (e.g., a thin, clear plastic film). The shield 1404 can be sufficiently thin to reduce or avoid interfering with sound transmission, e.g., when the user is speaking. For example, the shield 1404 can be no more than 5 mm, 4.5 mm, 4 mm, 3.5 mm, 3 mm, 2.5 mm, 2 mm, 1.5 mm, 1 mm, 0.75 mm, 0.5 mm, 0.25 mm, or 0.1 mm in thickness. Optionally, the frame 1402 can hold the shield 1404 in tension so that shield 1404 maintains a desired shape (e.g., a flat shape, a curved shape, etc.). In the illustrated embodiment, the frame 1402 extends along all four edges of the shield 1404. In other embodiments, however, the frame 1402 can extend along only some of the edges of the shield 1404, e.g., only the upper and lower edges, only the lateral edges, only a single edge, etc.

The respirator devices described herein can include additional components. For example, any of the mask sections or shield described herein can include one or more openings to allow administration of medicines, drinks, and the like. The opening can be sufficiently large to allow a drinking straw, pills, and/or other medicines to be administered to the user, yet not too large such that the device can no longer maintain the desired pressure level.

As another example, the devices herein can include one or more sensors to monitor the operation of the mask (e.g., pressure levels, air flow, temperature, air quality), the user's condition (e.g., body temperature, respiratory rate, pulse, blood pressure), and/or user compliance (e.g., whether the user is wearing the device properly). Examples of sensors suitable for use within the devices described herein include, but are not limited to: pressure sensors, flow sensors, temperature sensors, air quality sensors, breath sensors, blood pressure sensors, heart rate sensors, blood oxygenation sensors, audio sensors, image sensors, light sensors, and/or combinations thereof.

In some embodiments, the respirator devices described herein are designed to be disinfected and reused, e.g., using cleaning and/or sterilization techniques known to those of skill in art such as applying disinfectant, heat treatment, washing, etc. Optionally, the devices herein, or individual components thereof (e.g., mask section, shield, frame, etc.) can include an antimicrobial surface, coating, or material to further reduce the risks of transmission when worn, donning, doffing, disinfecting, or otherwise being handled. In other embodiments, however, the devices disclosed herein can be designed to be single-use, disposable devices.

In some embodiments, the respirator devices described herein include an alert system which can provide the user and/or others with feedback, e.g., on compliance, system integrity, and/or the user's physiological condition. The alert system can include, for example, visual alerts (e.g., LED lighting), audible alerts (e.g., tones, spoken instructions), and/or haptic alerts (e.g., buzzing). Alerts can also be communicated to a separate device (e.g., a device carried by the user or another individual, such as a smartphone, smartwatch, tablet, laptop computer, personal computer, etc.) via wired or wireless communication methods (e.g., Bluetooth). For example, an alert may be triggered if a user takes off their device in a certain location in a hospital. The alert can include an audible alert, a color change in the device's lighting system, and/or a notification of the user's location transmitted to healthcare personnel. Advantageously, if a contamination or infection event were to occur, relevant personnel could be instantaneously informed and contact tracing could be implemented where relevant. As another example, an alert may be triggered by changes and/or errors in device operation, such as a change in pressure or the inability of the device to maintain negative pressure. In a further example, an alert may be triggered by changes in the user's condition, such as a lack of rise and fall in pressure consistent with breathing.

In some embodiments, the respirator devices described herein are configured to monitor the status of filters, source control mechanisms, and/or other sanitization mechanisms. For example, each filter can be associated with an identifier (e.g., an RFID tag), and the device can include electronic components (e.g., an RFID reader) configured to detect, identify, and/or authenticate the identifier to confirm that the filter is suitable for use. If the filter cannot be identified or authenticated, or is otherwise not suitable for use, the device can notify the user, e.g., via an alert system. As another example, the device can monitor and provide feedback on the status of filters during operation (e.g., whether the filter has reached its capacity, the time period since the filter was last replaced, etc.).

The sanitization mechanisms described herein (e.g., filters, source control mechanisms) can be provided in cartridges, housings, or other packaging components allowing them to be handled without touching the components that contact infectious matter (e.g., the filter material), thus reducing transmission risk during removal, replacement, donning, doffing, wearing, and/or other handling operations.

In some embodiments, the respirator devices described herein are used to reduce or prevent transmission of an infectious disease, such as COVID-19. For example, any of the respirator devices described herein can be used to filter, inactivate, eradicate, etc. SARS-CoV-2 from an air flow (e.g., air exiting the respirator device to an external environment and/or air entering the respirator device from the external environment). SARS-CoV-2 (and/or matter containing SARS-CoV-2 such as aerosolized droplets) can be removed from an air flow using any of the filters, source control mechanisms, and/or other sanitization mechanisms described herein, including fibers (e.g., nanofibers), electrostatic, ultraviolet, chemical, temperature, ozone, magnetic, ionizing, ionizing-magnetic, and/or ionizing-electrostatic sanitization mechanisms. The respirator devices herein can be configured to remove and/or inactivate at least 75%, 80%, 90%, 95%, 99%, 99.5%, 99.9%, 99.99%, or 99.999% of SARS-CoV-2 (and/or matter containing SARS-CoV-2) from ingoing and/or outgoing air flows. Accordingly, the respirator devices herein can be worn by individuals who are known or suspected to be infected with SARS-CoV-2 to reduce or prevent the transmission of COVID-19. Additionally, the respirator devices herein can be worn by individuals who may come in contact with infected persons to protect such individuals from contracting COVID-19.

E. EXAMPLES

The following examples are included to further describe some aspects of the present technology, and should not be used to limit the scope of the invention.

Example 1: Source Control Mask with Sealing Flaps: A user is a patient in a hospital and has a communicable disease. As such, the user has put on a source control mask to avoid transmitting the infectious agent to the health care workers. The source control mask being worn by the user is a powered source control mask with spring-loaded sealing flaps (e.g., similar to FIGS. 7A and 7B).

During normal tidal breathing, the source control mask scrubs the exhaled air as the user breathes out. In this case, the user is breathing at 18 breaths per minute and at a tidal volume of 500 ml. This gives a total exhalation volume or respiratory minute volume of 9 L/m. The user has a peak exhalation rate of 30 L/min. At this breathing rate, the extraction rate of the fan is set at 50 L/min. The air pressure in the mask is set at negative 5 Pa and this is measured by the air pressure gauge inside the mask. An algorithm is used to set the speed and hence the extraction rate of the fan to maintain this pressure. The mask is maintained at a constant negative pressure to ensure that all exhaled air is extracted and sterilized across the filter. The constant pressure within the mask is maintained below atmospheric pressure to ensure that the air flow across the engineered air gap always flows inwards.

The user's breathing rate then increases as a response to activity to 22 breaths per minute. The tidal volume also increases to 600 ml, and hence the respiratory minute volume rate increases to 13.2 L/min and the peak exhalation rate increases to 41 L/min. The source control mask detects the rise in pressure from −5 Pa to −3.5 Pa inside the mask and the fan speed is increased to provide an extraction rate of 60 L/min. At this rate, the minimum pressure of −5 Pa in the mask is maintained across the breathing cycle and this ensures no exhaled air is allowed to escape across the air gap and thus infect the atmospheric air. During normal breathing the inflowing air across the air gap holds the spring-loaded flaps up and prevents them from touching the user's face. During this time, all the air being exhaled is being sterilized by passing through a nanofiber filter that filters 99.99% of viruses and bacteria and provides a resistance of 60 Pa at 60 L/min.

The user then coughs and the peak exhalation rate sharply rises to a peak of 300 L/min. The pressure in the mask rises to a peak pressure of 200 Pa. At this moment, the air flow in the mask starts to reverse and the airflow across the gap slows, stops, and then reverses. As the airflow across the gap slows, the sealing flaps close under spring tension. The flaps then seal the mask and contain the expelled coughed air, preventing infectious material from escaping. The rise in pressure is measured by a pressure sensor and the fans are switched to full power. The flap gives the fan time to ramp up to 200 L/min, and the air from the contained cough is extracted and passed across the filter.

As the pressure inside the mask during this time is over the atmospheric pressure, the air in the mask moves naturally across the filter under its own energy which assists the fan in extracting the air and returning the mask to a safe negative pressure. This occurs two seconds after the cough and the flaps open up, allowing the atmospheric air to flow back into the mask.

Example 2: Expandable Source Control Mask: The user is a worker in an industrial workplace and has influenza that they do not want to pass on to their co-workers via a respiratory vector. They put on a source control mask (e.g., similar to FIGS. 3A and 8B). This is a powered source control mask that also acts as an air-purifying respirator. The mask forms a tight-fitting seal around the user's mouth and nose. The mask is firmly fitted to the user with the use of head straps.

As the worker is operating a grinder at work and producing large amounts of hazardous particulate matter, respiratory protection is required to the standard of N95. The source control mask is filtering the inhaled air and the exhaled air, and acts as both an N95 mask and as a source control mask. The worker must regularly walk into other areas of the workshop to pick up tools or to pick up new work pieces of material. It is during this time that they are in danger of transmitting the influenza to their co-workers who are not masked.

The worker is breathing at an elevated rate of 22 breaths per minute due to their physical exertion and at a tidal volume of 800 ml per breath, thus giving a respiratory minute volume of 9 L/min. The extraction fan does not need to meet peak exhalation rates as the seal contains the peak exhaled air. The fan is set at an extraction rate of 14 L/min which gives an average pressure inside the mask of −2 Pa. This pressure gradient produces a constant flow into the mask of purified air and scrubs the exhaled breath as the user breathes out. This avoids the discomfort of rebreathing a portion of their last breath, along with an increase in oxygen supply and a decrease in carbon dioxide when rebreathing.

The user produces a cough when they are picking up a part from the storage rack where other co-workers are present. In a conventional mask, this would break the seal and allow infected air to pass into the atmosphere and create an infection hazard. During the cough event, the pressure in the user's mouth sharply rises to 200 Pa and the peak exhalation rate rises to 350 L/min.

As the pressure in the mask rises, the elastic and flexible portion of the mask bulges out under this pressure from 92 $cm^3$ to 205 $cm^3$ and contains the coughed air in this increased volume. The airflow across the filter reverses as the pressure inside the mask is greater than atmospheric pressure. The reversed airflow and the expansion work in conjunction to limit the rise in pressure. The mask pressure rises to 140 Pa. This prevents the seal from being broken as the pressure required to break the seal is 170 Pa which is greater than the pressure required to expand the mask. The pressure inside the mask produces an air flow across the filter, which is working in conjunction with the fan to extract the air in the mask. Since the flexible portion of the mask is elastic in nature, the mask returns to its normal size as the pressure drops under 60 Pa.

Even if the power to the mask fails, the mask would still continue to work as designed to filter inhaled and exhaled air since no air can enter or leave the mask without passing through the filter.

Several aspects of the present technology are set forth in the following additional examples:

1. A source control mask device comprising:
   a face mask having a frame and a shield, the shield being configured to cover at least a mouth and nose of a user's face and defining at least a portion of a breathing chamber, wherein the face mask is configured to form an engineered gap spacing a periphery of the face mask apart from the user's face;
   a powered impeller unit carried by the face mask and configured to create an area of low pressure in the breathing chamber, wherein the powered impeller unit is configured such that atmospheric air continually enters the breathing chamber across the engineered gap for the prevention of infected air from entering the atmosphere; and
   a sanitation assembly in fluid communication with the breathing chamber and configured to receive air extracted from the breathing chamber and to eradicate or reduce infectious agents in the extracted air.

2. The source control mask device of example 1 wherein the powered impeller unit comprises fans configured to create an area of low pressure in the breathing chamber relative to atmospheric pressure.

3. The source control mask device of example 1 or example 2 wherein the face mask is configured to deflect the exhaled air downward, and wherein the shield is shaped to deflect the exhaled air back through the sanitation assembly with the air exiting behind the user's face.

4. The source control mask device of any one of the preceding examples wherein the sanitation assembly comprises a filter component, and wherein air extracted from the breathing chamber is configured to pass across the filter component to eradicate or reduce at least one infectious agent.

5. The source control mask device of any one of the preceding examples wherein the engineered gap between the face mask and the user's face is sized according to a size of the breathing chamber and airflow extraction is configured to be greater than expelled air during user exhalation or coughing.

6. The source control mask device of any one of the preceding examples wherein the powered impeller unit comprises at least one having configured to create an extraction rate greater than an exhalation rate of the user such that the source control mask device provides an area of lower pressure than atmospheric air in the breathing chamber.

7. The source control mask device of example 6, further comprising sensors on the face mask for monitoring relative pressure between the breathing chamber and atmosphere, and wherein the source control mask device is configured to adjust extraction rate maintain a negative pressure.

8. The source control mask device of any one of the preceding examples, further comprising a battery unit carried by the face mask and coupled to the powered impeller unit and the sanitation assembly.

9. The source control mask device of any one of the preceding examples wherein the powered impeller unit is configured such that air enters the breathing chamber through the engineered gap in an approximately even radial flow.

10. The source control mask device of any one of the preceding examples wherein the face mask comprises expansion blow flaps.

11. The source control mask device of example 10 wherein the expansion blow flaps are configured to be held open by inrushing air, and wherein the expansion blow flaps close shut to form a seal when pressure in the breathing chamber falls to approximately zero.

12. The source control mask device of any one of the preceding examples, further comprising a sensor to detect a cough and/or a sneeze.

13. The source control mask device of example 12 wherein the sensor is configured to measure pressure in the breathing chamber, and wherein the face mask further includes an electronically operated seal configured to operate if the pressure detected via the sensor reaches a threshold of approximately negative 5 Pa.

14. The source control mask device of example 12, further comprising a controller operably coupled to the sensor and configured to predict an oncoming cough or sneeze by sensing and detecting a sharp intake of breath.

15. The source control mask device of any one of the preceding examples wherein the sanitation assembly comprises a sanitization medium selected from any one of the following: fibrous, nanofiber, electrostatic, ultraviolet, chemical, ozone, ionizing, ionizing-magnetic, and/or ionizing-electrostatic.

16. The source control mask device of any one of the preceding examples wherein the face mask is configured to filter incoming and outgoing air.

17. The source control mask device of any one of the preceding examples wherein the face mask comprises an expandable material, and wherein the expandable material is pleated or elastic and configured to expand during a cough or sneeze event.

18. The source control mask device of any of the preceding examples wherein the shield is a double shield including an inner shield and an outer shield, and wherein the inner shield is removable.

19. The source control mask device of any one of the preceding examples wherein the shield is clear.

20. The source control mask device of any one of the preceding examples, wherein the shield is manufactured out of a thin plastic film held in tension by the frame, and wherein the frame is rigid.

21. The source control mask device of any one of the preceding examples wherein the shield comprises at least one aperture to allow administration of medicines and/or drinks to the user's face.

22. The source control mask device of any one of the preceding examples, further comprising physiological sensors carried by the face mask.

23. The source control mask device of any one of the preceding examples wherein the mask monitors and provides feedback on the filter status during sanitization/sterilization.

24. The source control mask device of any one of the preceding examples wherein the sanitation assembly comprises filter cartridges configured in a manner for contactless removal and replacement.

25. The source control mask device of any one of the preceding examples wherein the face mask is manufactured using an antimicrobial surface, coating or material.

26. The source control mask device of any one of the preceding examples wherein the face mask includes an alert system configured to provide feedback on mask compliance, system integrity and the user's physiological state.

27. The source control mask device of example 26 wherein the alert system is configured to be triggered by any one of the following: a change in pressure or the inability of the mask to maintain negative pressure or a lack of rise and fall in pressure consistent with breathing.

28. A source control attachment for a respirator mask comprising:
- a strip of material for fastening to the perimeter of a mask shield; and
- at least one filter component,
- wherein, the source control attachment is configured to be substantially located around the mask shield and seal to the mask shield and a user's face to allow air to flow out of the higher pressure shield into the atmosphere while filtering, eradicating or reducing any infectious agents contained within the expelled air of the mask as it is breathed out by the user.

29. The source control attachment of example 28 wherein the attachment or skirt is utilized as an attachment to a non-seal continuous flow respirator or equivalent flow mask device similar to a PAPR.

30. The source control attachment of example 29 wherein the mask shield comprises a firmware mode for when using the source control attachment during a higher peak internal pressure during exhalation.

31. The source control attachment of example 28 wherein the source control attachment comprises a soft dermatologically friendly, non-porous strip that touches the face.

32. The source control attachment of any one of the preceding examples, wherein the mask shield and the source control attachment inactivate any one of the following: viruses, fungi, bacteria and/or combinations of the following filtration of the mucosalivary droplet, droplet nuclei, and or skin cells etc. by sieving, impaction on the fibers, diffusion onto the fibers, electrostatic attraction, and or magnetic attraction onto the fibers.

33. The source control mask and attachment of any one of the preceding examples, wherein inactivation of a pathogen occurs through any one of the following methods or mechanisms: ozone, contact with the fiber, electric discharge, ultraviolet light, chemical, temperature, electrostatic precipitation and/or magnetic attraction.

34. A respirator device, comprising:
- a mask section comprising a shield and defining a breathing chamber, wherein the mask section is configured to fit at least partially over a user's face with a gap spacing a periphery of the mask section apart from the user's face;
- a source control mechanism in fluid communication with the breathing chamber and configured to sanitize air exiting from the breathing chamber to an external environment; and
- a fan unit configured to maintain a negative pressure relative to the external environment within the breathing chamber and an air flow path through the breathing chamber, the air flow path including (i) an air inflow entering the breathing chamber via the gap and (ii) an air outflow exiting the breathing chamber via the source control mechanism.

35. The respirator device of example 34 wherein the source control mechanism is configured to filter SARS-CoV-2 from air exiting the breathing chamber to the external environment.

36. The respirator device of example 34 or example 35, further comprising a pressure sensor configured to detect a pressure level in the breathing chamber, wherein the fan unit is configured to adjust an air outflow rate based on the detected pressure level.

37. The respirator device of any one of examples 34-36 wherein the source control mechanism includes a filter configured to obstruct an infectious agent from entering the external environment.

38. The respirator device of any one of examples 34-37 wherein the source control mechanism includes the fan unit.

39. The respirator device of any one of examples 34-38 wherein the air outflow has a flow rate greater than an exhalation flow rate of the user during one or more of the following: breathing, talking, coughing, or sneezing.

40. The respirator device of any one of examples 34-39, further comprising a sealing member coupled to the mask section at or near the gap, wherein the sealing member is movable between an open configuration and a closed configuration.

41. The respirator device of example 40 wherein the sealing member is configured to move from the open configuration to the closed configuration when a pressure level in the breathing chamber increases above a threshold.

42. The respirator device of example 41 wherein the sealing member is configured to remain in the closed configuration until the pressure level falls below the threshold.

43. The respirator device of any one of examples 40-42, wherein the sealing member is configured to move from the open configuration to the closed configuration in response to one or more of the following: a detected cough, a predicted cough, a detected sneeze, or a predicted sneeze.

44. A respirator device, comprising:
- a mask section comprising a shield and defining a breathing chamber, wherein the shield is configured to fit at least partially over a user's face;
- an intake section coupled to the mask section and configured to sanitize air entering the breathing chamber from an external environment;
- a source control member extending at least partly around the mask section and configured to sanitize air exiting from the breathing chamber to the external environment; and
- a fan unit configured to maintain a positive pressure relative to the external environment within the breathing chamber and an air flow path through the breathing chamber, the air flow path including (i) an air inflow entering the breathing chamber via the intake section and (ii) an air outflow exiting the breathing chamber via the source control member.

45. The respirator device of example 44 wherein the source control member is configured to filter SARS-CoV-2 from air exiting the breathing chamber to the external environment.

46. The respirator device of example 44 or example 45 wherein the source control member includes a filtering material configured to seal against the user's face.

47. The respirator device of any one of examples 44-46 wherein the source control member is removably coupled to the mask section.

48. The respirator device of any one of examples 44-47 wherein the intake section includes an inlet filter and the source control member includes an outlet filter.

49. The respirator device of example 48 wherein the outlet filter has different properties than the inlet filter.

50. The respirator device of example 49 wherein the outlet filter has a greater pore size than the inlet filter.

51. The respirator device of any one of examples 44-50 wherein the source control member includes an active sanitization mechanism.

52. The respirator device of example 51 wherein the active sanitization mechanism is configured to use one or more of the following: ozone, electric discharge, electrostatic attraction, electrostatic precipitation, magnetic attraction, chemical inactivation, or temperature inactivation.

53. A respirator device, comprising:
a mask section comprising a shield and defining a breathing chamber, wherein the shield is configured to fit at least partially over a user's face;
an intake region fluidly coupled to the breathing chamber;
a source control mechanism fluidly coupled to the breathing chamber and configured to sanitize air exiting from the breathing chamber to an external environment; and
at least one fan unit configured to maintain an air flow path through the breathing chamber, the air flow path including (i) an air inflow entering the breathing chamber via the intake region and (ii) an air outflow exiting the breathing chamber via the source control mechanism.

54. The respirator device of example 53 wherein the at least one fan unit is configured to maintain a negative pressure relative to the external environment within the breathing chamber.

55. The respirator device of example 53 wherein the at least one fan unit is configured to maintain a positive pressure relative to the external environment within the breathing chamber.

56. The respirator device of any one of examples 53-55 wherein at least 95% of the air exiting from the breathing chamber passes through the source control mechanism.

57. The respirator device of any one of examples 53-56 wherein the source control mechanism comprises a filter.

58. The respirator device of any one of examples 53-57 wherein the source control mechanism comprises an active sanitation mechanism configured to use one or more of the following: ozone, electric discharge, electrostatic attraction, electrostatic precipitation, magnetic attraction, chemical inactivation, or temperature inactivation.

59. The respirator device of any one of examples 53-58 wherein the source control mechanism is positioned at one or more following: a periphery of the mask section, a surface of the mask section, or a location spaced apart from the mask section.

60. The respirator device of any one of examples 53-59 wherein the source control mechanism includes the at least one fan unit.

61. The respirator device of any one of examples 53-60 wherein the intake region includes a filter configured to sanitize air entering the breathing chamber from the external environment.

62. The respirator device of any one of examples 53-61, further comprising an adjustable region included in or coupled to the mask section, wherein the adjustable region is adapted to change in configuration based on a pressure level within the mask section.

63. The respirator device of any one of examples 53-62, further comprising at least one sensor, wherein an air outflow rate produced by the at least one fan unit is variable based on data generated by the sensor.

64. A method of reducing transmission of an infectious disease, comprising:
positioning the respirator device of any one of examples 34-63 at least partially over a face of an individual with the infectious disease; and
sanitizing air exhaled by the individual with the respirator device.

65. The method of example 64, wherein the infectious disease is COVID-19.

F. CONCLUSION

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

The embodiments described above may also be said broadly to consist in the parts, elements and features referred to or indicated in the specification of the application, individually or collectively, and any or all combinations of any two or more said parts, elements or features.

Further, where specific integers are mentioned herein which have known equivalents in the art to which the embodiments relate, such known equivalents are deemed to be incorporated herein as if individually set forth.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A respirator device, comprising:
a mask section comprising a shield and defining a breathing chamber, wherein the mask section is configured to fit at least partially over a user's face with a periphery of the mask section aligned with the user's mouth and/or nose and spaced apart from the user's mouth and/or nose by a gap;
an intake section coupled to the mask section and configured to sanitize air entering the breathing chamber from an external environment;
a source control member extending at least partly around the mask section and configured to extend across the gap between the periphery of the mask section and the user's face when the respirator device is worn by the user, the source control member being further configured to remove SARS-CoV-2 from air exiting from the breathing chamber to the external environment via the gap; and
a fan unit configured to maintain a positive pressure relative to the external environment within the breathing chamber and an air flow path through the breathing chamber, the air flow path including (i) an air inflow entering the breathing chamber via the intake section and (ii) an air outflow exiting the breathing chamber via the gap and the source control member.

2. The respirator device of claim 1 wherein the source control member is configured to remove SARS-CoV-2 from the air exiting the breathing chamber by filtering droplets containing SARS-CoV-2 from the air exiting the breathing chamber.

3. The respirator device of claim 1 wherein the source control member includes a filtering material configured to seal against the user's face.

4. The respirator device of claim 1 wherein the source control member is removably coupled to the mask section.

5. The respirator device of claim 1 wherein the intake section includes an inlet filter and the source control member includes an outlet filter.

6. The respirator device of claim 5 wherein the outlet filter has different properties than the inlet filter.

7. The respirator device of claim 6 wherein the outlet filter has a greater pore size than the inlet filter.

8. The respirator device of claim 1 wherein the source control member includes an active sanitization mechanism.

9. The respirator device of claim 8 wherein the active sanitization mechanism is configured to use one or more of the following: ozone, electric discharge, electrostatic attraction, electrostatic precipitation, magnetic attraction, chemical inactivation, or temperature inactivation.

10. A respirator device, comprising:
a mask section comprising a shield and defining a breathing chamber, wherein the mask section is configured to fit at least partially over a user's face with a periphery of the mask section aligned with the user's mouth and/or nose and spaced apart from the user's mouth and/or nose by a gap;
an intake region fluidly coupled to the breathing chamber;
a source control mechanism fluidly coupled to the breathing chamber and configured to extend across the gap between the periphery of the mask section and the user's face when the respirator device is worn by the user, the source control member being further configured to remove SARS-CoV-2 from air exiting from the breathing chamber to an external environment via the gap; and
at least one fan unit configured to maintain an air flow path through the breathing chamber, the air flow path including (i) an air inflow entering the breathing chamber via the intake region and (ii) an air outflow exiting the breathing chamber via the gap and the source control mechanism.

11. The respirator device of claim 10 wherein the at least one fan unit is configured to maintain a negative pressure relative to the external environment within the breathing chamber.

12. The respirator device of claim 10 wherein the at least one fan unit is configured to maintain a positive pressure relative to the external environment within the breathing chamber.

13. The respirator device of claim 10 wherein at least 95% of the air exiting from the breathing chamber passes through the source control mechanism.

14. The respirator device of claim 10 wherein the source control mechanism comprises a filter.

15. The respirator device of claim 10 wherein the source control mechanism comprises an active sanitation mechanism configured to use one or more of the following: ozone, electric discharge, electrostatic attraction, electrostatic precipitation, magnetic attraction, chemical inactivation, or temperature inactivation.

16. The respirator device of claim 10 wherein the source control mechanism includes the at least one fan unit.

17. The respirator device of claim 10 wherein the intake region includes a filter configured to sanitize air entering the breathing chamber from the external environment.

18. The respirator device of claim 10, further comprising an adjustable region included in or coupled to the mask section, wherein the adjustable region is adapted to change in configuration based on a pressure level within the mask section.

19. The respirator device of claim 10, further comprising at least one sensor, wherein an air outflow rate produced by the at least one fan unit is variable based on data generated by the sensor.

20. A respirator device, comprising:
a mask section comprising a shield and defining a breathing chamber, wherein the mask section is configured to fit at least partially over a user's face with a periphery of the mask section aligned with the user's mouth and/or nose and spaced apart from the user's mouth and/or nose by a gap;
an intake region fluidly coupled to the breathing chamber;
a source control mechanism fluidly coupled to the breathing chamber and configured to extend across the gap between the periphery of the mask section and the user's face when the respirator device is worn by the user, the source control member being further configured to sanitize air exiting from the breathing chamber to an external environment via the gap; and
at least one fan unit configured to maintain an air flow path through the breathing chamber, the air flow path including (i) an air inflow entering the breathing chamber via the intake region and (ii) an air outflow exiting the breathing chamber via the gap and the source control mechanism.

21. The respirator device of claim 20 wherein the source control mechanism comprises a filter.

22. The respirator device of claim 20 wherein the source control mechanism comprises an active sanitation mechanism configured to use one or more of the following: ozone, electric discharge, electrostatic attraction, electrostatic precipitation, magnetic attraction, chemical inactivation, or temperature inactivation.

23. The respirator device of claim 20 wherein the air inflow is a first air inflow positioned on a first side of the breathing chamber, the air flow path further including a second air inflow positioned on a second side of the breathing chamber.

\* \* \* \* \*